US010213546B2

(12) United States Patent
Anderson et al.

(10) Patent No.: US 10,213,546 B2
(45) Date of Patent: Feb. 26, 2019

(54) DEVICES AND METHODS FOR DELIVERING A BENEFICIAL AGENT TO A USER

(71) Applicant: ABBVIE INC., North Chicago, IL (US)

(72) Inventors: Phil Anderson, Libertyville, IL (US); Kevin Novak, Park Ridge, IL (US); Kevin McLennan, Chicago, IL (US); Michael Mackaplow, Chicago, IL (US); Guiyong Song, Libertyville, IL (US); Gurjinder Singh Dhami, Neenah, WI (US); Benjamin Alan Jasperson, Greenville, WI (US); Scott Smieja, Oshkosh, WI (US); Matthew Svacina, Little Chute, WI (US)

(73) Assignee: ABBVIE INC., North Chicago, IL (US)

( * ) Notice: Subject to any disclaimer, the term of this patent is extended or adjusted under 35 U.S.C. 154(b) by 374 days.

(21) Appl. No.: 15/064,481

(22) Filed: Mar. 8, 2016

(65) Prior Publication Data
US 2016/0184507 A1     Jun. 30, 2016

Related U.S. Application Data

(63) Continuation-in-part of application No. PCT/US2014/072979, filed on Dec. 31, 2014, which
(Continued)

(51) Int. Cl.
*A61M 5/14*        (2006.01)
*A61M 5/142*       (2006.01)

(52) U.S. Cl.
CPC ........ *A61M 5/142* (2013.01); *A61M 5/14228* (2013.01); *A61M 5/14244* (2013.01);
(Continued)

(58) Field of Classification Search
CPC .............. A61M 5/14228; A61M 5/142; A61M 5/14244; A61M 2205/12; A61M 2205/121
See application file for complete search history.

(56) References Cited

U.S. PATENT DOCUMENTS

| 4,493,706 A * | 1/1985 | Borsanyi ............... A61M 5/142 |
| | | 128/DIG. 12 |
| 4,537,561 A | 8/1985 | Xanthopoulos |
| | | (Continued) |

FOREIGN PATENT DOCUMENTS

| EP | 1393762 A1 * | 3/2004 | ........ A61M 5/14232 |
| JP | 2005 351131 A | 12/2005 | |

OTHER PUBLICATIONS

English translation of EP 1393762.*
(Continued)

*Primary Examiner* — Nathan R Price
*Assistant Examiner* — Courtney Fredrickson
(74) *Attorney, Agent, or Firm* — Baker Botts L.L.P.

(57) ABSTRACT

A device for delivering a beneficial agent is provided and generally includes a cassette, a pump, and a delivery tube. The pump includes a pump housing containing a pump assembly having a fluid drive component. The pump housing has a receiving region disposed proximate the fluid drive component and further includes a rear closure portion. The rear closure portion includes a membrane disposed between the receiving region and the fluid drive component. The cassette includes a cassette housing, which has a cassette body region defining a fluid reservoir chamber therein. The cassette further includes a cassette base region having a boundary configured to be received by the receiving region.

12 Claims, 35 Drawing Sheets

Related U.S. Application Data is a continuation of application No. 14/586,912, filed on Dec. 30, 2014, and a continuation of application No. 14/586,916, filed on Dec. 30, 2014.

(60) Provisional application No. 61/922,721, filed on Dec. 31, 2013, provisional application No. 62/054,153, filed on Sep. 23, 2014.

(52) U.S. Cl.
CPC ...... *A61M 2205/12* (2013.01); *A61M 2205/123* (2013.01); *A61M 2205/6027* (2013.01); *A61M 2205/6054* (2013.01); *A61M 2205/8206* (2013.01)

(56) References Cited

U.S. PATENT DOCUMENTS

| | | |
|---|---|---|
| 5,131,816 A | 7/1992 | Brown et al. |
| 5,181,910 A | 1/1993 | Scanlon |
| D348,730 S | 7/1994 | Walker et al. |
| 5,397,222 A | 3/1995 | Moss et al. |
| 5,538,399 A | 7/1996 | Johnson |
| D376,796 S | 12/1996 | Hirasawa |
| 5,620,312 A | 4/1997 | Hyman et al. |
| 5,718,562 A | 2/1998 | Lawless et al. |
| 5,755,691 A | 5/1998 | Hilborne |
| 5,928,196 A | 7/1999 | Johnson et al. |
| 5,935,099 A | 8/1999 | Peterson et al. |
| 6,077,055 A | 6/2000 | Vilks |
| D439,341 S | 3/2001 | Tumey et al. |
| 6,227,203 B1 | 5/2001 | Rise et al. |
| 6,243,117 B1 | 6/2001 | Brandon et al. |
| 6,305,908 B1 | 10/2001 | Hermann et al. |
| 6,371,732 B1 | 4/2002 | Moubayed et al. |
| 6,422,057 B1 | 7/2002 | Anderson |
| D471,562 S | 3/2003 | Kagami et al. |
| D471,917 S | 3/2003 | Kagami et al. |
| D482,370 S | 11/2003 | Niwatsukino et al. |
| D484,146 S | 12/2003 | Urano et al. |
| 6,742,992 B2 | 6/2004 | Davis |
| D517,091 S | 3/2006 | Sugiyama et al. |
| 7,018,361 B2 | 3/2006 | Gillespie, Jr. et al. |
| D520,023 S | 5/2006 | Goto et al. |
| D520,024 S | 5/2006 | Chen |
| D566,131 S | 4/2008 | Detering et al. |
| D579,569 S | 10/2008 | Strawn et al. |
| D583,856 S | 12/2008 | Mizuno et al. |
| D585,543 S | 1/2009 | Yodfat et al. |
| 7,628,770 B2 | 12/2009 | Ethelfeld |
| D626,647 S | 11/2010 | Amborn et al. |
| 7,927,306 B2 | 4/2011 | Cross et al. |
| 8,114,066 B2 | 2/2012 | Naef et al. |
| D655,810 S | 3/2012 | Amborn et al. |
| D659,717 S | 5/2012 | Mattson et al. |
| 8,298,184 B2 | 10/2012 | DiPerna et al. |
| D675,252 S | 1/2013 | Harvey et al. |
| 8,377,002 B2 | 2/2013 | Hanson et al. |
| D687,140 S | 7/2013 | Guarraia et al. |
| D689,523 S | 9/2013 | Galbraith et al. |
| D697,204 S | 1/2014 | Maier et al. |
| D720,804 S | 1/2015 | Van Den Broecke |
| D725,678 S | 3/2015 | Sekula et al. |
| 8,974,415 B2 | 3/2015 | Robert et al. |
| D744,005 S | 11/2015 | Anderson et al. |
| D744,586 S | 12/2015 | Chung et al. |
| D746,441 S | 12/2015 | Harr et al. |
| D746,871 S | 1/2016 | Anderson et al. |
| D776,253 S | 1/2017 | Li |
| 2003/0233069 A1 | 12/2003 | Gillespie et al. |
| 2004/0051368 A1 | 3/2004 | Caputo et al. |
| 2005/0094485 A1 | 5/2005 | Demers et al. |
| 2007/0078377 A1 | 4/2007 | Mason |
| 2008/0091139 A1 | 4/2008 | Srinivasan et al. |
| 2008/0255516 A1 | 10/2008 | Yodfat et al. |
| 2009/0182265 A1 | 7/2009 | Mason |
| 2010/0049128 A1 | 2/2010 | McKenzie et al. |
| 2010/0143168 A1 | 6/2010 | Miyazaki et al. |
| 2011/0166511 A1 | 7/2011 | Sharvit et al. |
| 2011/0202005 A1 | 8/2011 | Yodfat et al. |
| 2011/0300010 A1 | 12/2011 | Jarnagin et al. |
| 2012/0053522 A1 | 3/2012 | Yodfat et al. |
| 2012/0191059 A1 | 7/2012 | Cummings et al. |
| 2012/0217276 A1 | 8/2012 | Kennedy |
| 2012/0277667 A1 | 11/2012 | Yodat et al. |
| 2013/0154252 A1* | 6/2013 | Rakowicz ............ F16L 35/00 285/18 |
| 2013/0267899 A1 | 10/2013 | Robert et al. |
| 2014/0194818 A1 | 7/2014 | Yodfat et al. |

OTHER PUBLICATIONS

U.S. Appl. No. 29/566,784, filed Jun. 2, 2016.
U.S. Appl. No. 29/513,435, Aug. 18, 2016 Response to Non-Final Office Action.
U.S. Appl. No. 29/513,437, Sep. 9, 2016 Notice of Allowance.
U.S. Appl. No. 29/513,437, Aug. 18, 2016 Response to Non-Final Office Action.
U.S. Appl. No. 29/513,438, Jun. 28, 2016 Notice of Allowance.
U.S. Appl. No. 29/513,438, May 26, 2016 Notice of Allowance.
U.S. Appl. No. 29/513,438, May 26, 2016 Issue Fee Payment.
International Search Report and Written Opinion dated Mar. 30, 2015 in International Application No. PCT/US2014/072973.
International Search Report and Written Opinion dated Mar. 30, 2015 in International Application No. PCT/US2014/072979.
U.S. Appl. No. 14/586,916, Oct. 6, 2017 Non-Final Office Action.
U.S. Appl. No. 14/586,912, Nov. 24, 2017 Non-Final Office Action.
U.S. Appl. No. 29/513,435, Dec. 14, 2016 Issue Fee Payment.
U.S. Appl. No. 29/513,437, Dec. 8, 2016 Issue Fee Payment.
U.S. Appl. No. 29/550,455, Dec. 6, 2017 Notice of Allowance.
U.S. Appl. No. 29/550,455, Nov. 2, 2017 Issue Fee Payment.
U.S. Appl. No. 29/550,455, Oct. 27, 2017 Notice of Allowance.
U.S. Appl. No. 29/550,455, Aug. 3, 2017 Notice of Allowance.
U.S. Appl. No. 29/566,784, Dec. 15, 2016 Issue Fee Payment.
U.S. Appl. No. 29/566,784, Dec. 7, 2016 Notice of Allowance.
U.S. Appl. No. 29/566,784, Nov. 2, 2016 Notice of Allowance.
U.S. Appl. No. 29/513,435, Sep. 15, 2016 Notice of Allowance.
U.S. Appl. No. 29/566,784, Sep. 16, 2016 Notice of Allowance.
U.S. Appl. No. 14/586,912 (US 2015/0182688), filed Dec. 30, 2014 (Jul. 2, 2015).
U.S. Appl. No. 14/586,916 (US 2015/0182689), filed Dec. 30, 2014 (Jul. 2, 2015).
U.S. Appl. No. 29/513,434 (D. 744,005), filed Dec. 30, 2014 (Nov. 24, 2015).
U.S. Appl. No. 29/513,435, filed Dec. 30, 2014.
U.S. Appl. No. 29/513,436 (D. 746,871), filed Dec. 30, 2014 (Jan. 5, 2016).
U.S. Appl. No. 29/513,437, filed Dec. 30, 2014.
U.S. Appl. No. 29/513,438, filed Dec. 30, 2014.
U.S. Appl. No. 29/550,455, filed Jan. 4, 2016.
U.S. Appl. No. 29/513,434, Oct. 20, 2015 Issue Fee Payment.
U.S. Appl. No. 29/513,434, Jul. 20, 2015 Notice of Allowance.
U.S. Appl. No. 29/513,436, Nov. 24, 2015 Issue Fee Payment.
U.S. Appl. No. 29/513,436, Aug. 24, 2015 Notice of Allowance.
U.S. Appl. No. 29/513,438, Feb. 26, 2016 Notice of Allowance.
U.S. Appl. No. 29/513,435, May 19, 2016 Non-Final Office Action.
U.S. Appl. No. 29/513,437, May 20, 2016 Non-Final Office Action.

\* cited by examiner

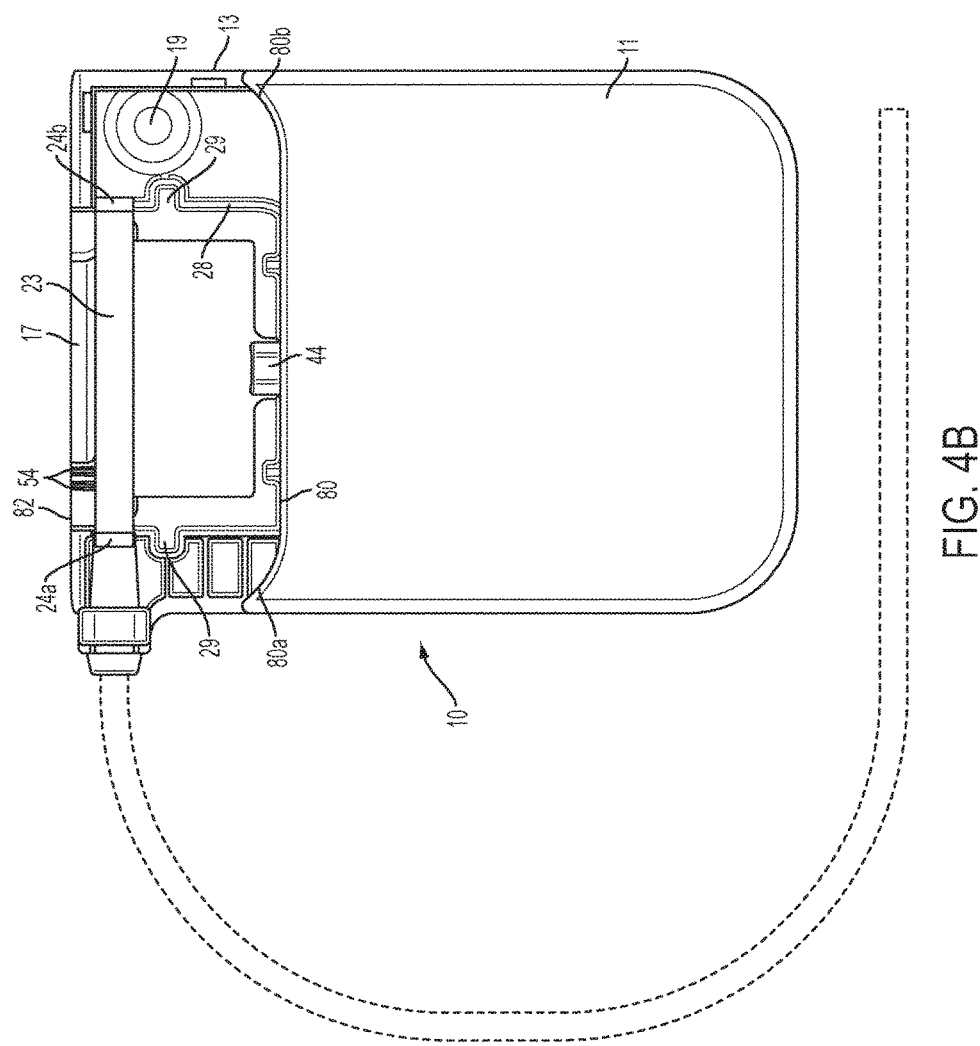

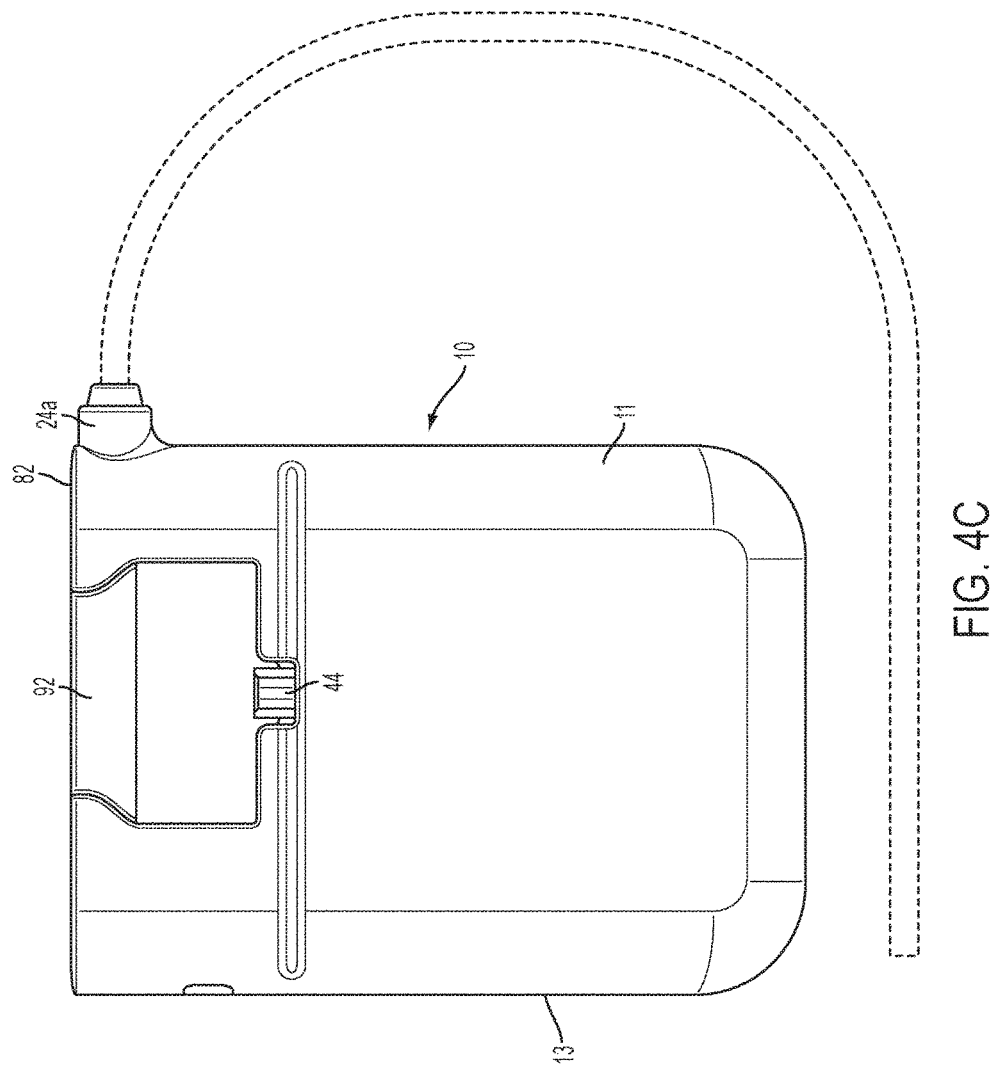

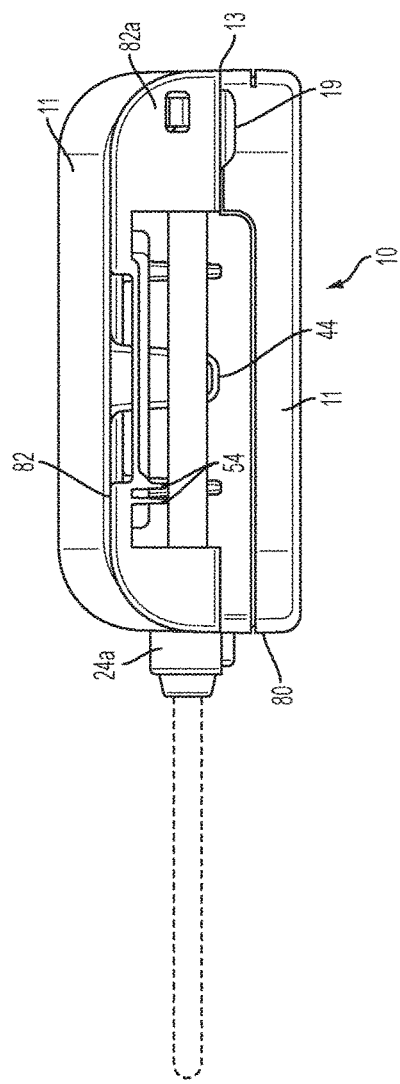
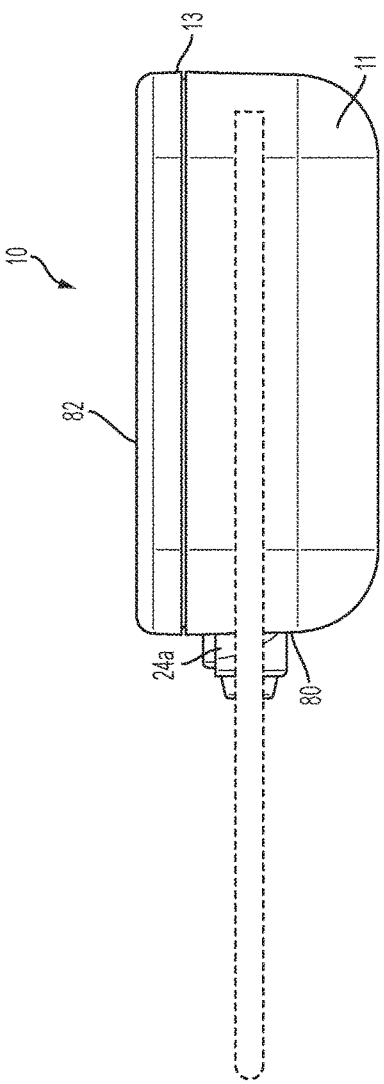

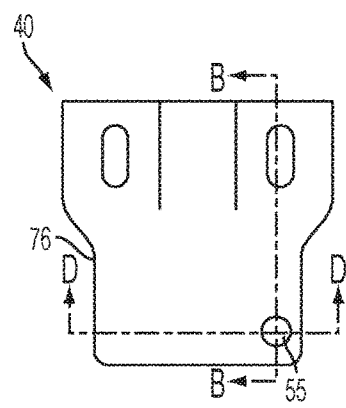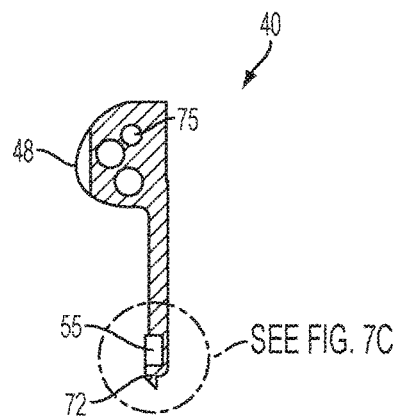
FIG. 7A  FIG. 7B
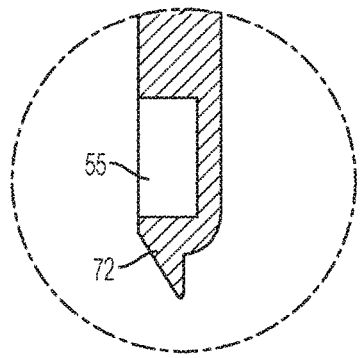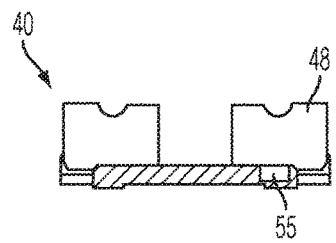
FIG. 7C  FIG. 7D
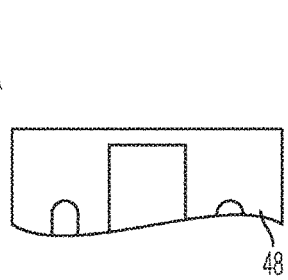
FIG. 7E

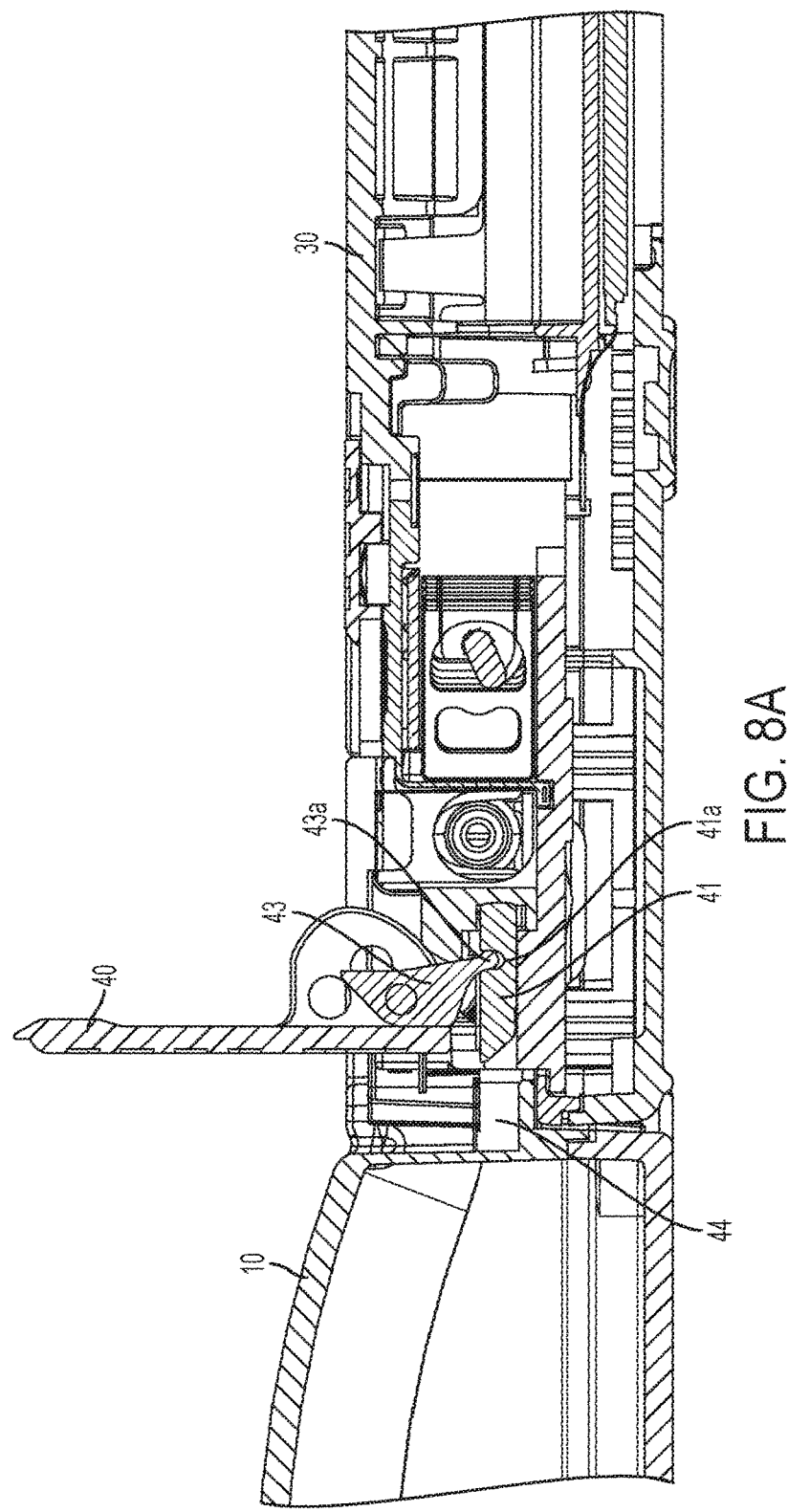

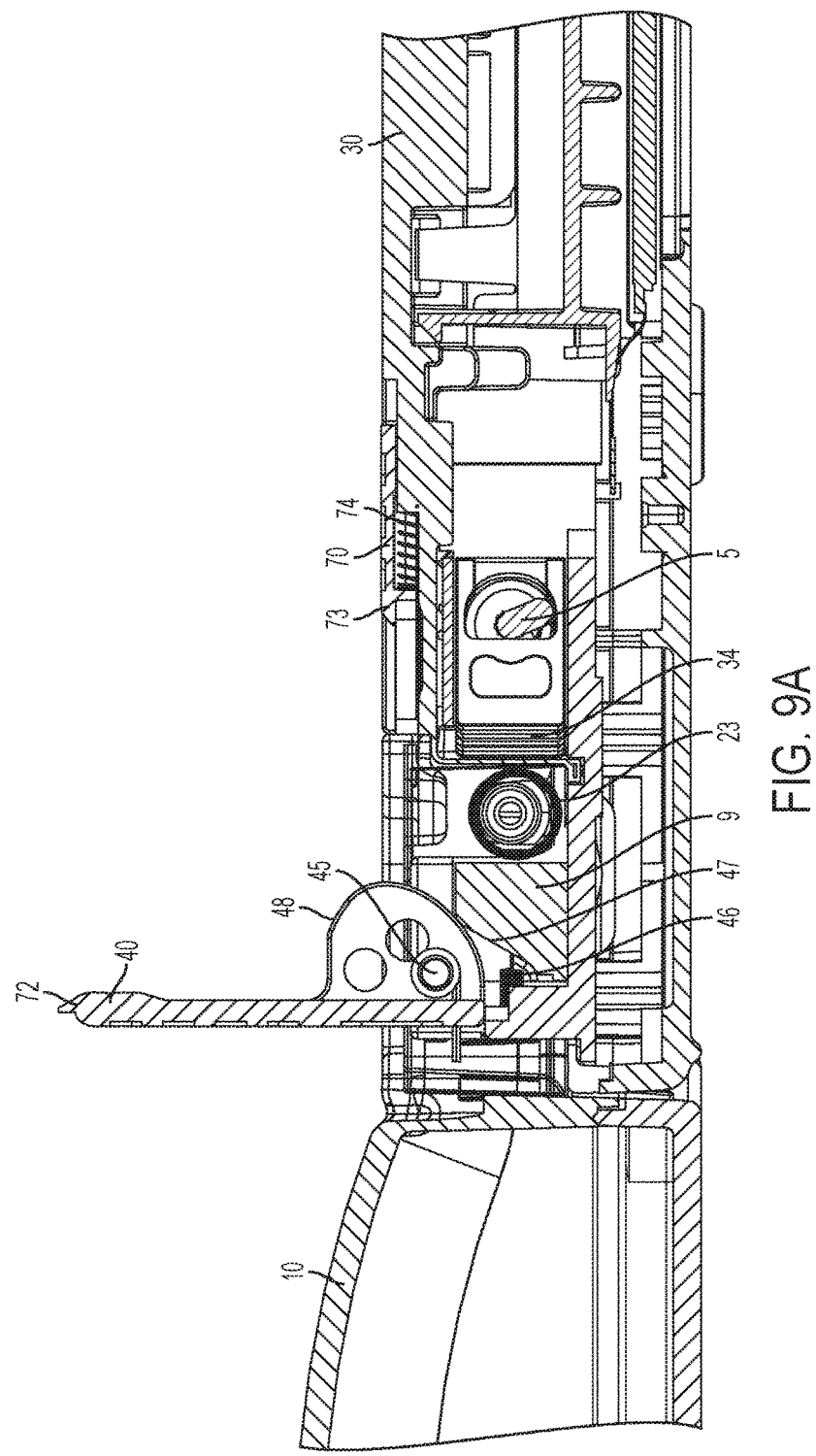

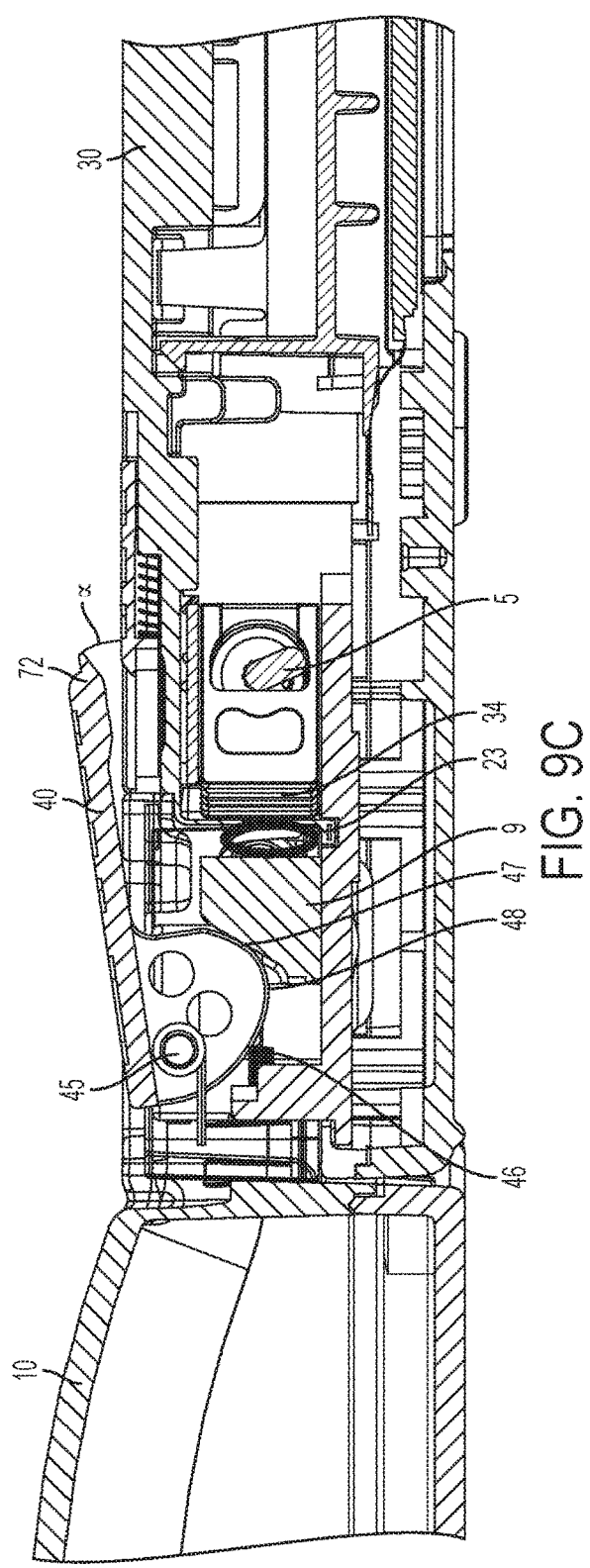

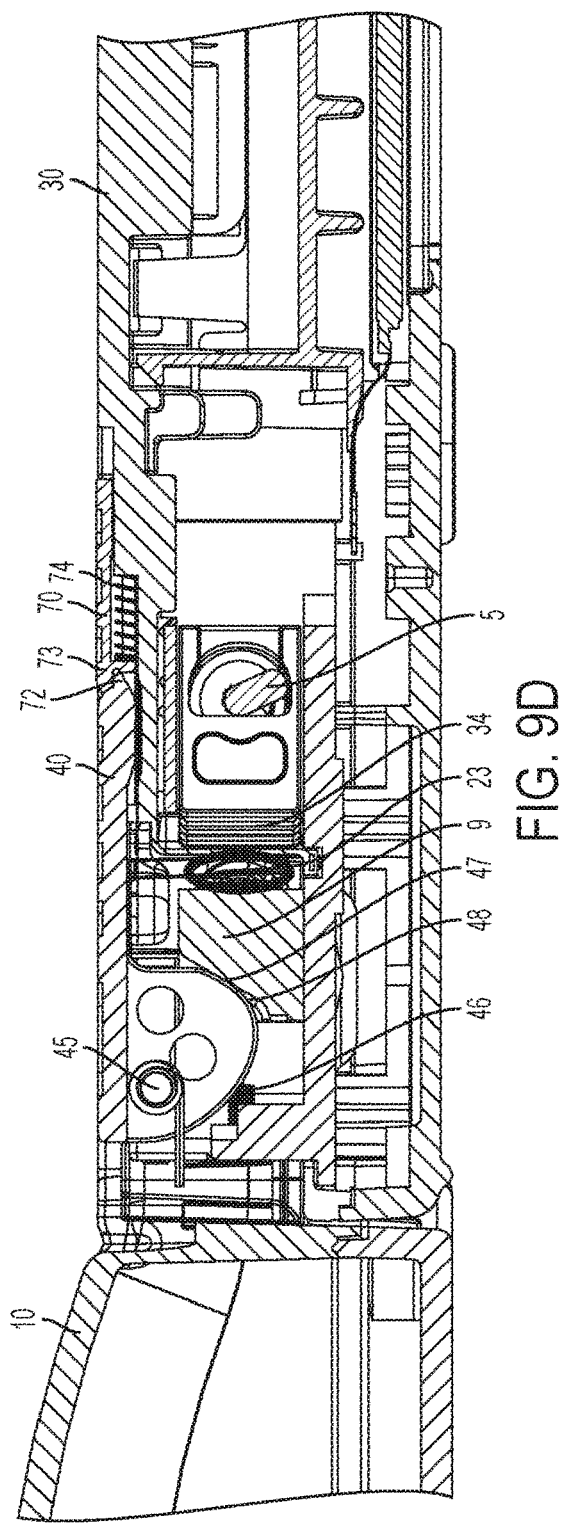

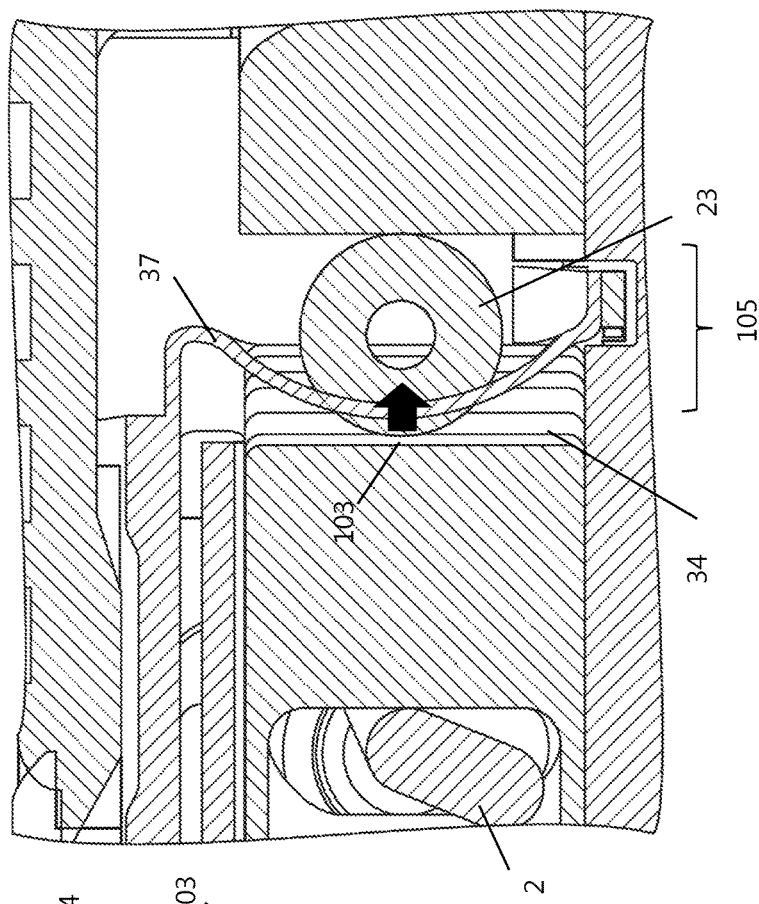
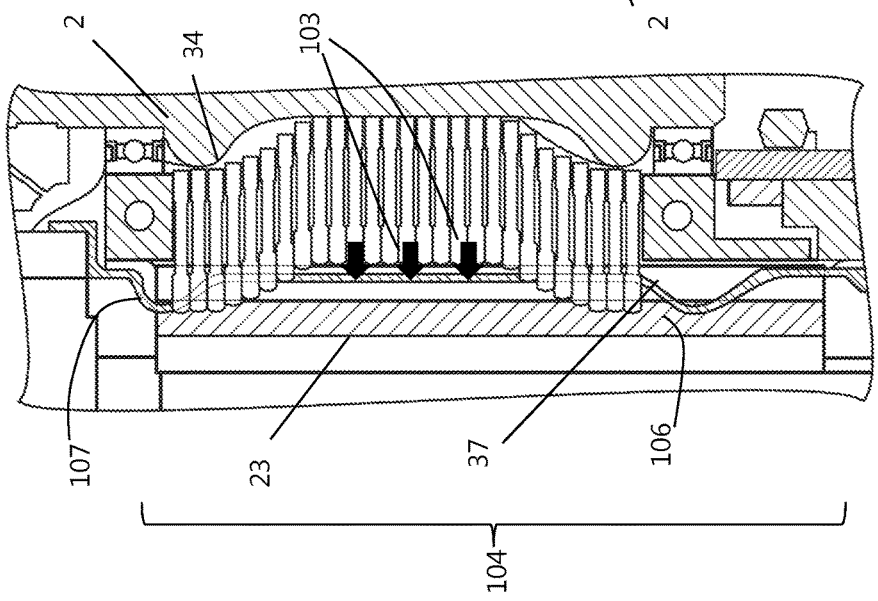

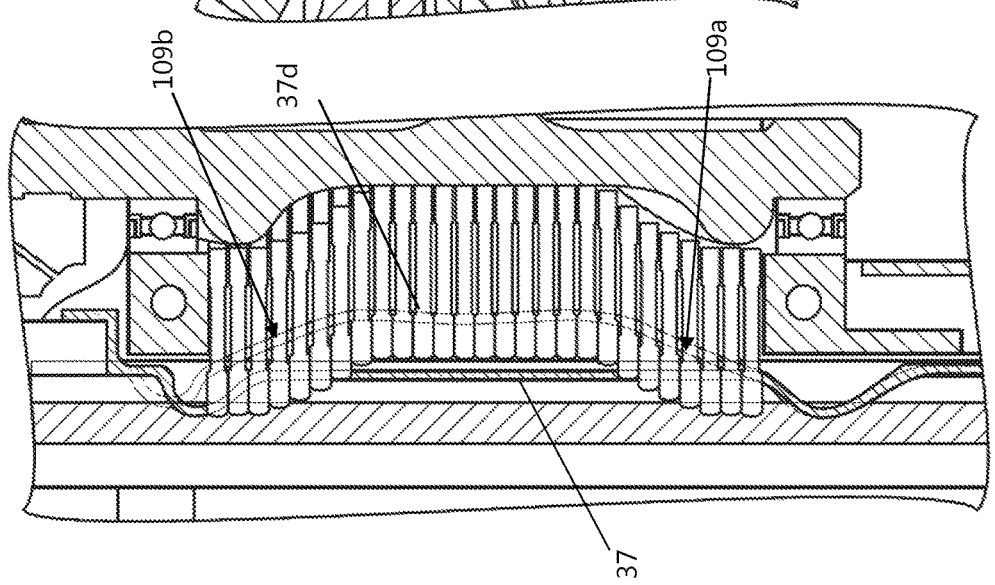
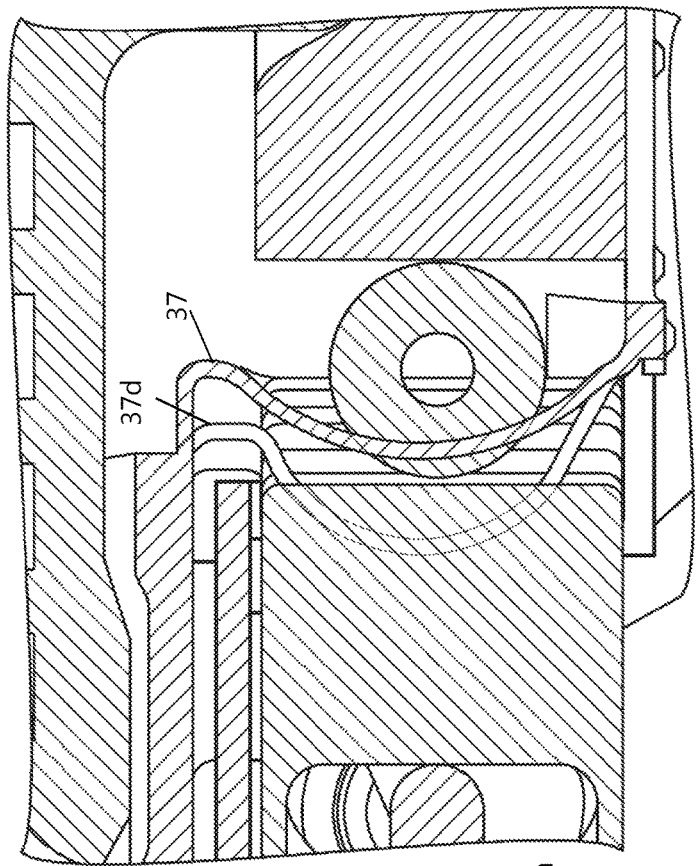
FIG. 11H
FIG. 11I

DEVICES AND METHODS FOR DELIVERING A BENEFICIAL AGENT TO A USER

CROSS-REFERENCE TO RELATED APPLICATIONS

This application is a continuation-in-part of PCT Application PCT/US2014/072979, which claims priority to U.S. Provisional Patent Application Nos. 61/922,721, filed Dec. 31, 2013; and 62/054,153, filed Sep. 23, 2014; and U.S. patent application Ser. No. 14/586,912, filed Dec. 30, 2014; and Ser. No. 14/586,916, filed Dec. 30, 2014; each of which is incorporated by reference herein in its entirety.

BACKGROUND

Field of the Disclosed Subject Matter

The disclosed subject matter relates to devices, systems and methods for controlling and delivering fluids, for example for delivery of a beneficial agent to a user.

Description of Related Art

A variety of fluid transport devices and systems have been developed for controlling and delivering beneficial agents in fluid form. Such fluid flow systems can include 1) volumetric-based aspiration flow systems using positive displacement pumps, and 2) vacuum-based aspiration systems using a vacuum source. For example, volumetric aspiration systems include peristaltic pumps for the delivery of therapeutic agents to a user. Various forms of peristaltic pumps are known, such as using rotating rollers to press against a flexible tubing to induce flow therethrough. Cassette systems or other reservoir configurations can be coupled with the pump to provide a source of beneficial agent fluid via the flexible tubing.

Such devices and systems are particularly beneficial as portable infusion pumps capable of being worn or carried by the user. However, there remains a need for improvement of such devices and systems. Such improvements include, among other things, improved energy consumption and battery life, improved pump efficiency and control, improved comfort and ergonomics, and improved cassette configuration for more complete access to the reservoir contents.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter provides a device for delivering a beneficial agent generally including a pump and a cassette. The pump includes a pump housing containing a pump assembly having a fluid drive component. The pump housing has a receiving region disposed proximate the fluid drive component and further includes a rear closure portion. The rear closure portion includes a membrane disposed between the receiving region and the fluid drive component. The cassette includes a cassette housing, which has a cassette body region defining a fluid reservoir chamber therein. The cassette further includes a cassette base region having a boundary configured to be received by the receiving region.

Additionally, and as embodied herein, the rear closure portion includes a slot proximate a lateral edge of the receiving region. The membrane can be molded over the slot and define a protrusion extending to said lateral edge of the receiving region. The slot includes a plurality of edges to support the membrane, and the membrane is molded over these edges. The receiving region further includes a support rib proximate to the rear closure portion. The membrane can also be molded over the support rib.

Furthermore, and as embodied herein, the fluid drive component includes a plurality of finger plates disposed along a length of a cam shaft. The finger plates can be configured to protrude from the slot to engage an interior surface of the membrane during rotation of the cam shaft. The cassette includes a delivery tube assembly extending from the fluid reservoir chamber. When the cassette base region boundary is received by the receiving region, the delivery tube assembly includes a peristaltic tube in functional relationship to the fluid drive component. The finger plates can be configured to engage the peristaltic tube with the membrane disposed between the plurality of finger plates and the peristaltic tube.

In addition, and as embodied herein, the membrane has a curvature corresponding to a curvature of the peristaltic tube. The peristaltic tube can be secured at an inlet end and an outlet end thereof, and the membrane can be configured to have a curvature proximate the inlet end and the outlet end corresponding to a position of the finger plates when the peristaltic tube is engaged by the finger plates at the inlet end and the outlet ends.

Additionally, and as embodied herein, when the cassette base region boundary is received by the receiving region, the peristaltic tube engages an occlusion sensor proximate the rear closure portion. The membrane can be configured to include an occlusion sensor protrusion configured to surround a portion of the occlusion sensor. The occlusion sensor protrusion can have a thickness greater than a remainder of the membrane.

Furthermore, and as embodied herein, any of the various devices and cassette can include a beneficial agent contained in the fluid reservoir. The beneficial agent can include one or more of levodopa and carbidopa.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIGS. 4A-4G are perspective, front, rear, left side, right side, top and bottom views, respectively, of an exemplary cassette of the device of FIG. 1.

FIG. 7A a bottom view of an exemplary lock member of the pump of FIG. 1.

FIG. 7B is a cross-sectional view of the exemplary lock member taken along line B-B of FIG. 7A.

FIG. 7C is a detailed view of region 7C of the cross section of the exemplary lock member of FIG. 7B.

FIG. 7D is a cross-sectional view of the exemplary lock member taken along line D-D of FIG. 7A.

FIG. 7E is a partial rear view of the exemplary lock member of FIG. 7A.

FIG. 8A is a cross-sectional view of the exemplary device taken along line 8A-8A of FIG. 2.

FIG. 9A is a cross-sectional view of the exemplary device taken along line 9A-9A of FIG. 2.

FIG. 9C is a cross-sectional view of the exemplary device of FIG. 9A, with the lock member urged further from the open position toward the closed position.

FIG. 9D is a cross-sectional view of the exemplary device taken along line 9D-9D of FIG. 3, with the lock member fully engaged.

FIGS. 11F and 11G are top and side views, respectively, of an exemplary embodiment of a membrane for a pump assembly in accordance with the disclosed subject matter.

FIGS. 11H and 11I are top and side views, respectively, of an alternative embodiment of the membrane of FIGS. 11F and 11G in accordance with the disclosed subject matter.

DESCRIPTION

Figure 1:
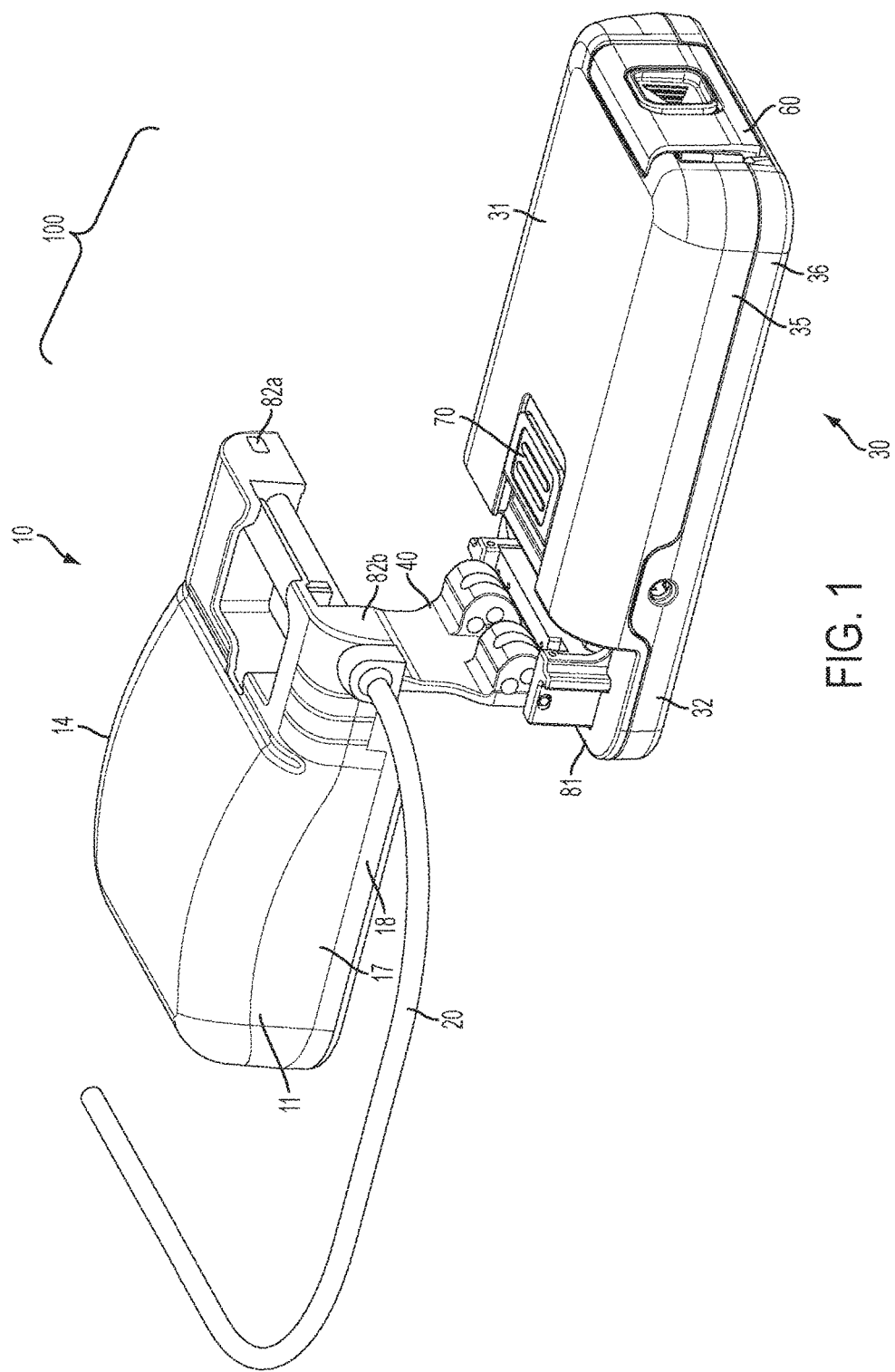
FIG. 1 is an exploded perspective view of an exemplary device for delivering a beneficial agent according to the disclosed subject matter.

Reference will now be made in detail to the various exemplary embodiments of the disclosed subject matter, exemplary embodiments of which are illustrated in the accompanying drawings. The structure and corresponding method of operation of and method of using the disclosed subject matter will be described in conjunction with the detailed description of the system.

The apparatus and methods presented herein can be used for administering any of a variety of suitable therapeutic agents or substances, such as a drug or biologic agent, to a patient. For example, and as embodied herein, the device can include a pump joined to a cassette, which can include a fluid reservoir containing a fluid substance and can be joined to a delivery tube system. In operation, the pump can operate on the cassette to deliver the fluid substance through the tubing system. In this manner, the device is capable of administering a dosage of the fluid substance, such as a therapeutic agent, including a formulation in a liquid or gel form, through the delivery tube system and to a patient. In some embodiments, the fluid therapeutic agent can include one or more pharmaceutical or biologic agents. For example and without limitation, one such fluid therapeutic agent can be a central nervous system agent, such as levodopa. The central nervous system agent can be administered alone or in combination with, for example and without limitation, a decarboxylase inhibitor, such as carbidopa.

According to subject matter disclosed herein, a device for delivering a beneficial agent is provided and generally includes a cassette, a pump, and a delivery tube. The pump includes a pump housing containing a pump assembly having a fluid drive component. The pump housing has a receiving region disposed proximate the fluid drive component and further includes a rear closure portion. The rear closure portion includes a membrane disposed between the receiving region and the fluid drive component. The cassette includes a cassette housing, which has a cassette body region defining a fluid reservoir chamber therein. The cassette further includes a cassette base region having a boundary configured to be received by the receiving region The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of the device for delivering a beneficial agent, including a drug delivery reservoir cassette, in accordance with the disclosed subject matter are shown in FIGS. 1-13.

While the disclosed subject matter is described with respect to a delivery device to administer a dose of therapeutic agent, one skilled in the art will recognize that the disclosed subject matter is not limited to the illustrative embodiment, and that the devices disclosed herein can be configured for delivering any suitable substance therethrough. In addition, the components and the method of using the delivery device are not limited to the illustrative embodiments described or depicted herein. For example, the delivery device embodied herein can be used with other tubing assemblies and components thereof for similar benefits and advantages, and are not limited for use with the delivery tubing herein.

Figure 2:
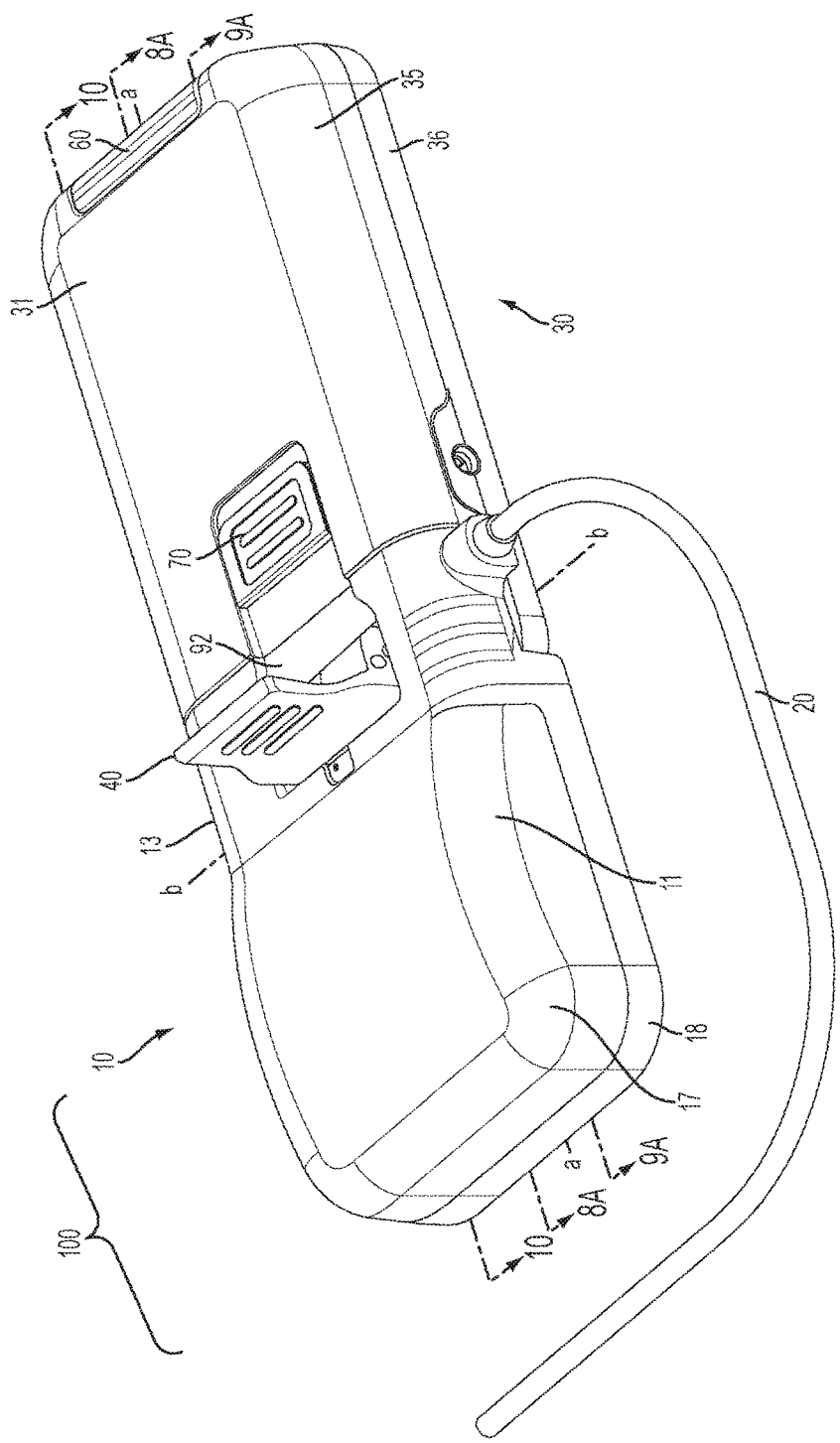
FIG. 2 is a perspective view of the device of FIG. 1, with the cassette received by the pump and the lock member in an open position.
Figure 3:
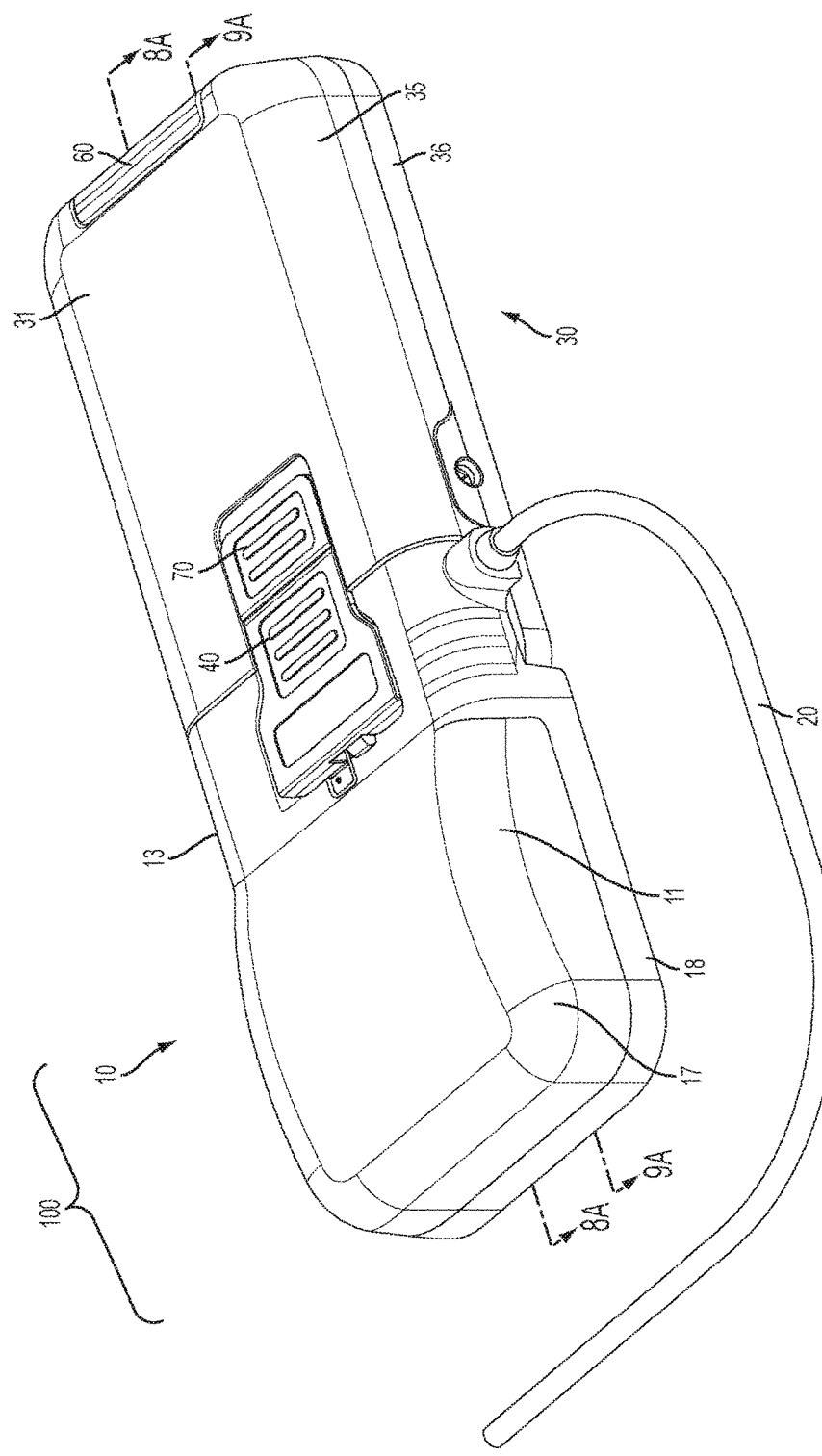
FIG. 3 is a perspective view of the device of FIG. 2, with the lock member in a closed position.
Figure 4A:
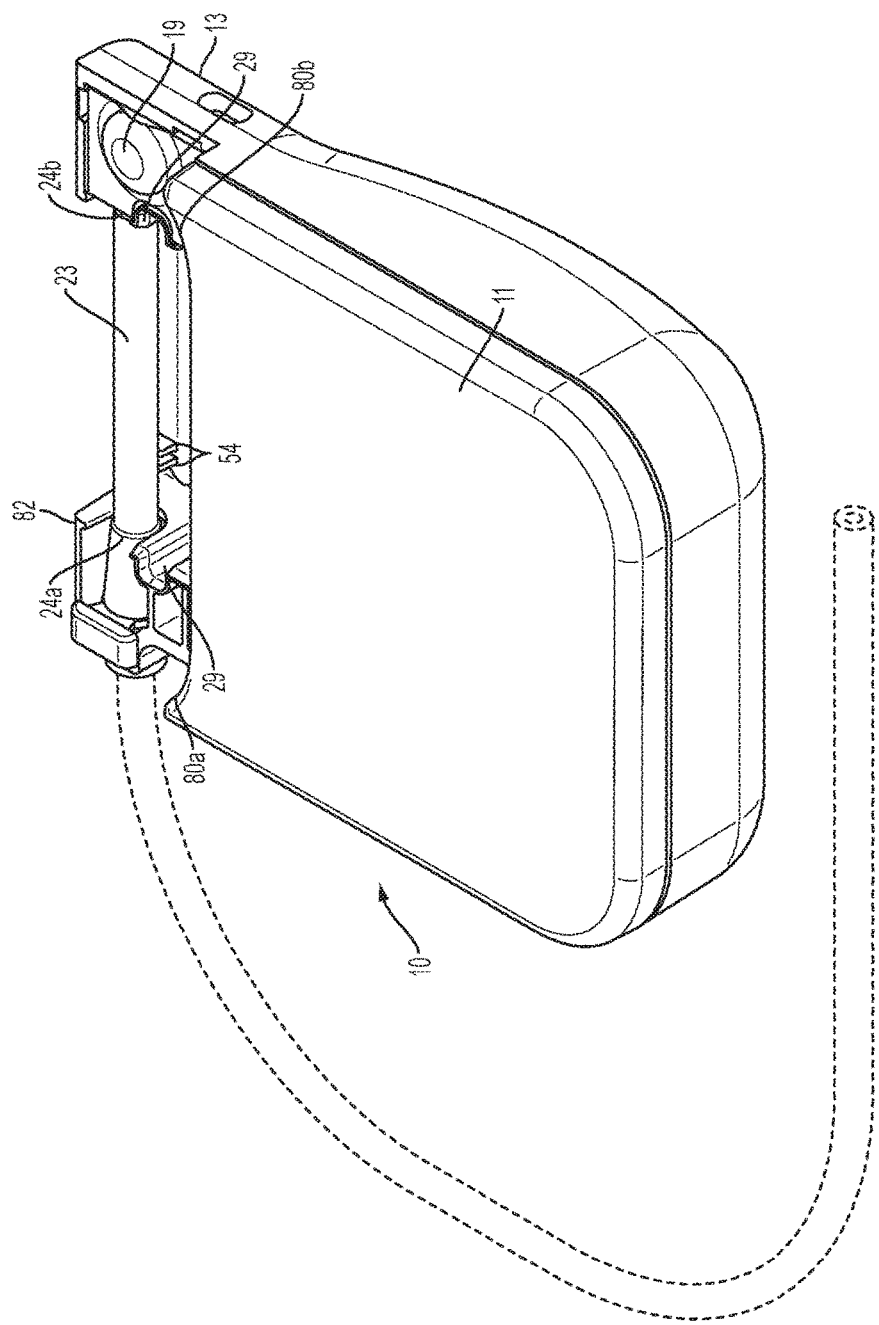
Figure 4D:
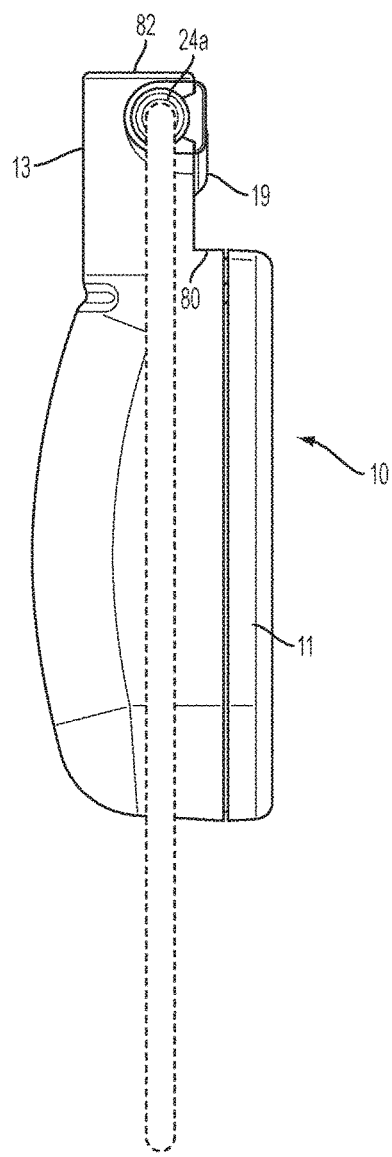
Figure 4E:
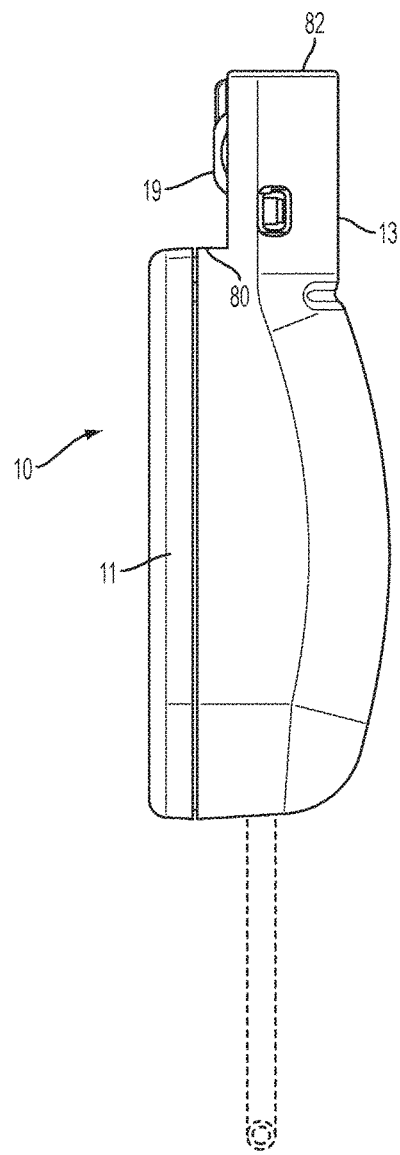

Referring to an illustrative embodiment of FIGS. 1-3, delivery device 100 includes a cassette 10 including a cassette housing 11. Cassette housing 11 can have a cassette body region 14. Cassette body region 14 can define an interior to contain a fluid reservoir 12 (shown for example in FIG. 13) within the cassette housing 11, as discussed further herein. Cassette body region 14 can be any suitable shape to accommodate a fluid reservoir 12. For example, and as embodied herein, cassette body region 14 can have a bulbous shape defining a curved surface proximate a back surface of the cassette housing 11, which can accommodate a fluid reservoir 12 having a similar size and shape. As embodied herein, cassette body region 14 can have a generally flat surface proximate front surface of cassette housing 11, opposite the back surface, which can allow cassette housing 11 to lay flat on a planar surface, such as a table, to facilitate a user to insert or remove cassette 10 from engagement with a pump 30, as discussed herein.

Furthermore, and as embodied herein, the cassette housing 11 can have a cassette base region 13 to join with the pump mechanism 30, as discussed further herein. As shown, for purpose of illustration and not limitation, cassette base region 13 can be disposed along a longitudinal axis, such as disposed along the longitudinal axis a from the cassette body region 14 defined along cassette 10.

The delivery device 100 also includes a pump 30, which can include a pump housing 31. With reference to FIGS. 1-3 and 5A-5G, the pump housing 31 can include a receiving region 32 to receive the cassette base region 13. For example, and as embodied herein, the receiving region can be disposed at one end of the pump 30. Referring now to FIGS. 1-3, the cassette base region 13 can be inserted into the receiving region 32 and secured to the pump 30 by closing lock member 40 into engagement with the cassette 10. As embodied herein, for illustration and not limitation, the lock member 40 is in the form of a lever, which closes over the cassette 10. In this manner, and as shown for example in FIGS. 9A-9D, the lock member 40 can also be configured to engage and secure peristaltic tube 23 to the pumping mechanism 30, as discussed further herein. The cassette 10 can be inserted into and removed from the receiving region 32 when the lock member 40 is in the open position. When the lock member 40 is in the closed position, the cassette 10 can be secured to the pump 30 with the cassette base region 13 disposed within the receiving region 32 and inhibited or prevented from disengagement from the pump 30.

Figure 5A:
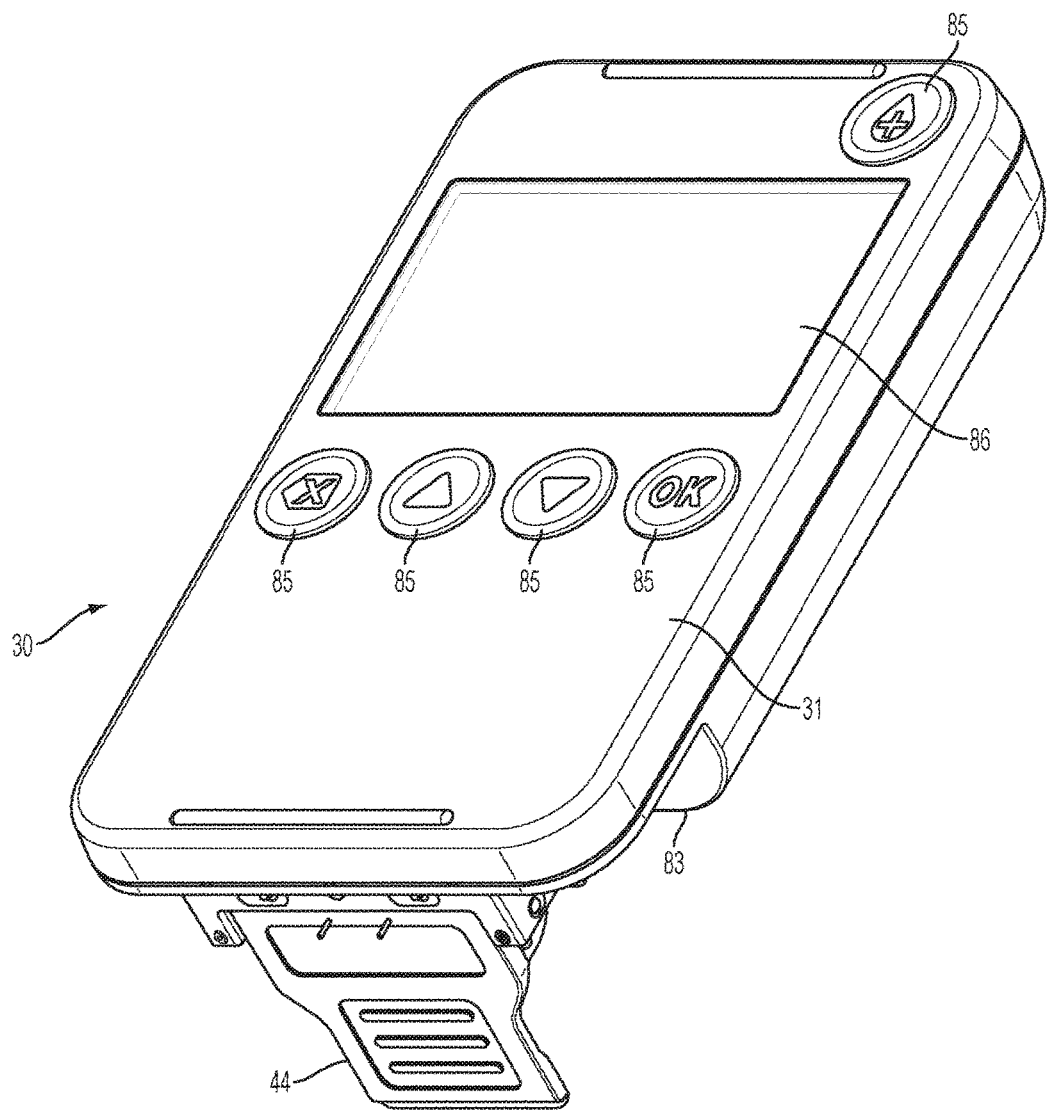
FIGS. 5A-5G are perspective, front, rear, left side, right side, top and bottom views, respectively, of an exemplary pump of the device of FIG. 1.
Figure 5B:
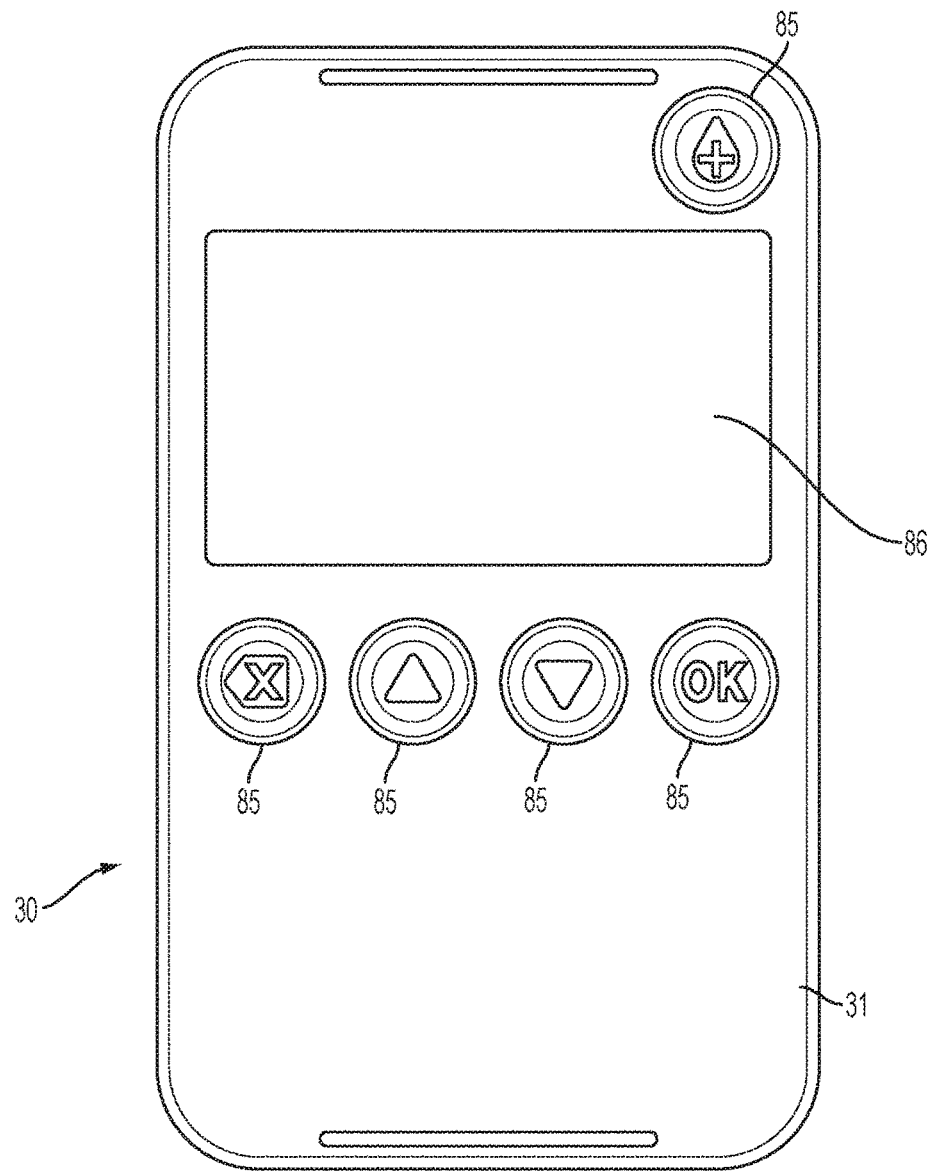

Additionally, with reference to FIGS. 5A-5B, pump housing 31 can include one or more inputs and outputs for interaction with a user. For example, and as embodied herein, pump housing 31 can include input buttons 85 disposed thereon, to provide, for example and without limitation, dosage settings and other device settings. Input buttons 85 can be formed using any suitable techniques. For example, and as embodied herein, input buttons 85 can be overmolded onto pump housing 31. Input buttons 85 can be formed of a material having a coefficient of static friction greater than that of the remainder of the pump housing 31, such as and without limitation, OM 3060-1 (GLS Corporation Versaflex®) and TM5ADT, TM6ADT and TM7ADT (each from Kraiburg TPE Corporation THERMOLAST®) which can, for example and without limitation, prevent sliding of pump housing 31 when disposed face down on a planar surface, such as a table, to facilitate a user to insert or remove cassette 10 from engagement with a pump 30, as discussed herein. Pump housing 31 can also include an output display 86. Output display 86 can be any suitable display to provide visual information to a user, for example and without limitation, an LCD or LED display or any other suitable display.

Referring now to FIGS. 4A-4G and 5A-5G, for the purpose of illustration and not limitation, the cassette 10 can be configured to be aligned and/or secured with the pump 30 via one or more features within the receiving region 32. For example, and as embodied herein, cassette base region 13 can define a boundary 28 to be received by receiving region 32 of the pump. As embodied herein, cassette base region 13 can include one or more rails 29 (as shown for example in FIG. 4B) configured to receive protrusions 33 of receiving region 32. As shown for example in FIG. 4B, cassette base region 13 can include a pair of opposing rails 29, which can be disposed on opposite sides of a longitudinal axis a defined by cassette 10, and can be substantially symmetrical about the longitudinal axis a. Additionally, and as embodied herein, each rail 29 can be recessed relative an adjacent portion of the boundary 28. As shown for purpose of illustration, rails 29 can be aligned along a transverse axis b defined across cassette 10. As embodied herein, each rail 29 can thus define an abutment surface generally parallel with the transverse axis b.

Figure 6:
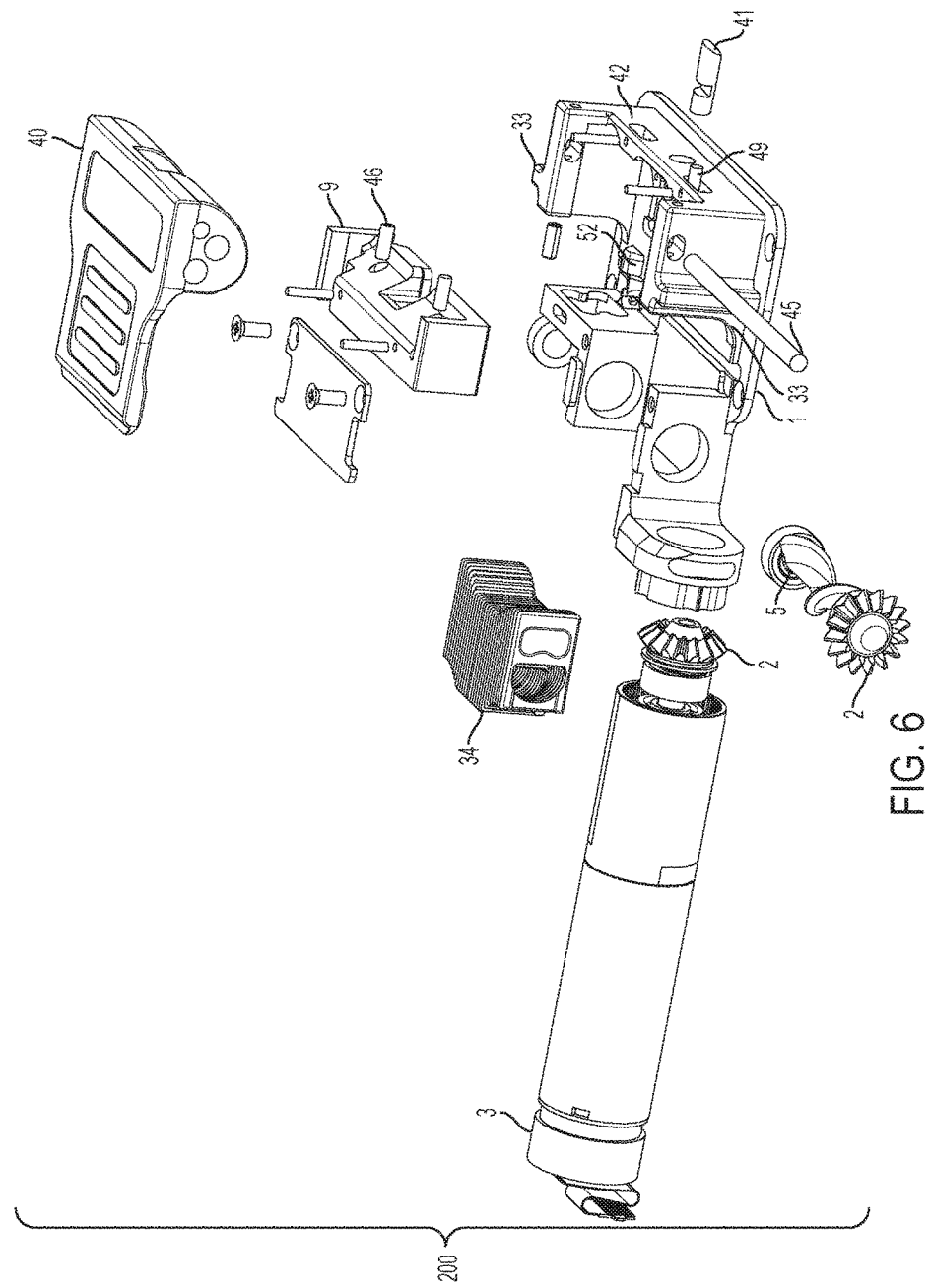
FIG. 6 is an exploded perspective view of an exemplary embodiment of a pump assembly in accordance with the disclosed subject matter.

Additionally, and as embodied herein, protrusions 33 to receive rails 29 can be formed in pump base block 1 (as shown for example in FIG. 6). For purpose of illustration, and as embodied herein, pump housing 31 can include one or more slots 39 (as shown for example in FIGS. 11A-11C) configured to receive protrusions 33 of the pump base block 1. Alternatively, the configuration of the rails and protrusions can be reversed, such that rails 29 are disposed on the cassette 10 and slots 39 are disposed on the pump 30.

Additionally or alternatively, and as embodied herein, the cassette 10 can be secured and aligned via an engagement surface 17, which can be received and captured by lock member 40 when in the closed position, as discussed further herein. Engagement surface 17 can be substantially coplanar with the back surface of the cassette housing 11. Alternatively, engagement surface 17 can include a recessed area 92 recessed relative the back surface of the cassette housing 17. For purpose of illustration, and as embodied herein, recessed area 92 can be shaped to receive and/or mate with at least a portion of lock member 40 when in the closed position, as shown for example in FIGS. 2-3. As such, and as embodied herein, recessed area 92 can taper to a smaller cross dimension toward an end 82 of the cassette housing 11, as shown for example in FIG. 4C. With reference to FIG. 4B, as embodied herein, the engagement surface 17 can be configured as an elongated strip of material to be engaged by lock member 40 when closed about engagement feature 17. In this manner, engagement surface 17 can form a unitary bridge across the longitudinal axis a. Alternatively, engagement surface 17 can include a pair of engagement surface portions on opposite sides of the longitudinal axis a, and in some embodiments, the pair of engagement surface portions can be substantially symmetrical about the longitudinal axis a.

Additionally or alternatively, and as embodied herein, the cassette 10 can be secured and aligned with the pump 30 via alignment pin 41 in the locking mechanism. As such, and as embodied herein, cassette base region 13 can include an alignment key 44 defining a receiving recess to receive alignment pin 41. For purpose of illustration and not limitation, and as embodied herein, alignment key 44 can be centered between the lateral side walls of cassette housing 11. As embodied herein, alignment key 44 can project into the boundary 28, and in some embodiments, alignment key 44 can project from the cassette body region 14 into the cassette base region 13. Alignment key 44 can have any suitable shape to receive alignment pin 41. For example and not limitation, alignment key 44 can be cylindrical, channel-shaped or any other suitable shape. Additionally or alternatively, as shown for example in FIG. 8B, the receiving recess formed by alignment key 44 can be tapered along the longitudinal axis to assist with receipt and alignment of alignment pin 41 therein.

Figure 5C:
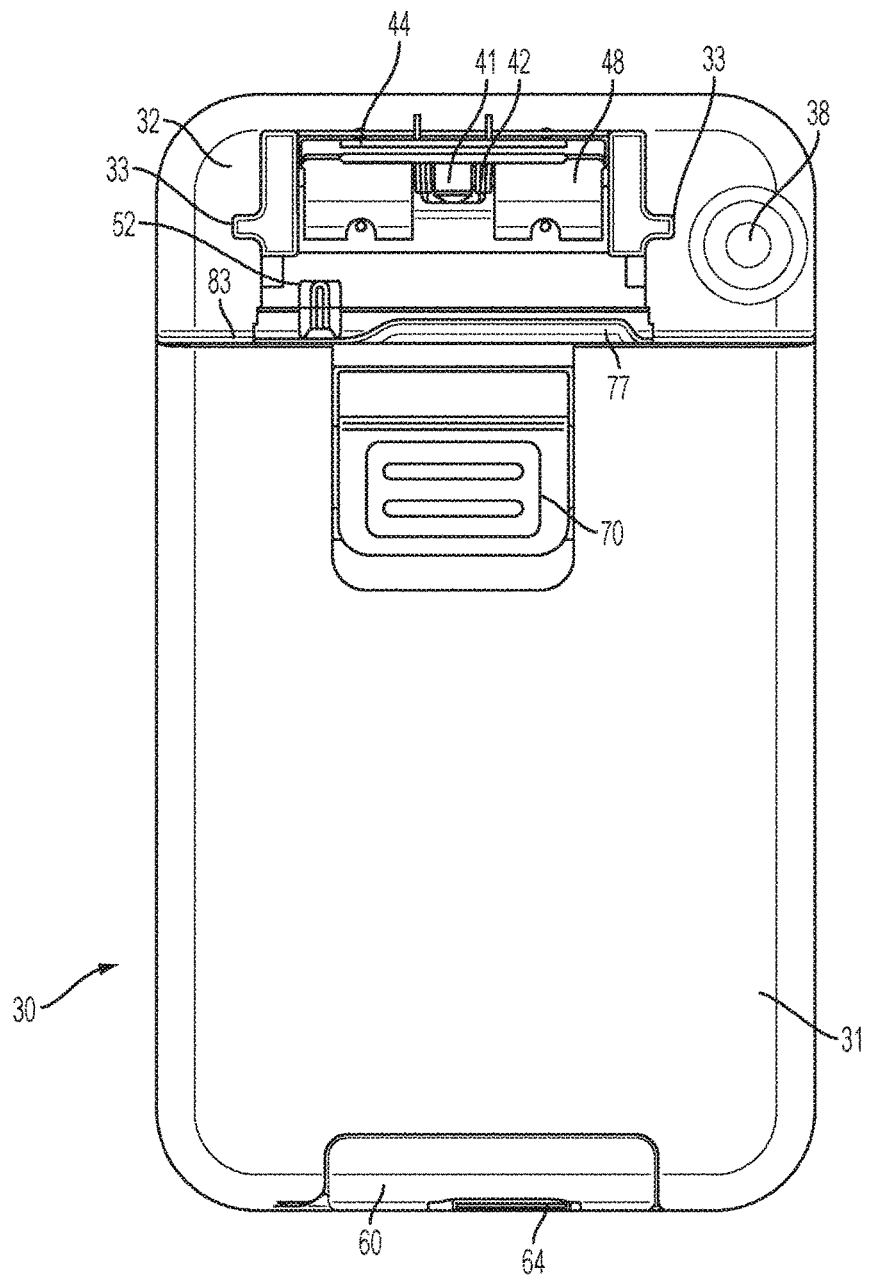
Figures 5D, 5E:
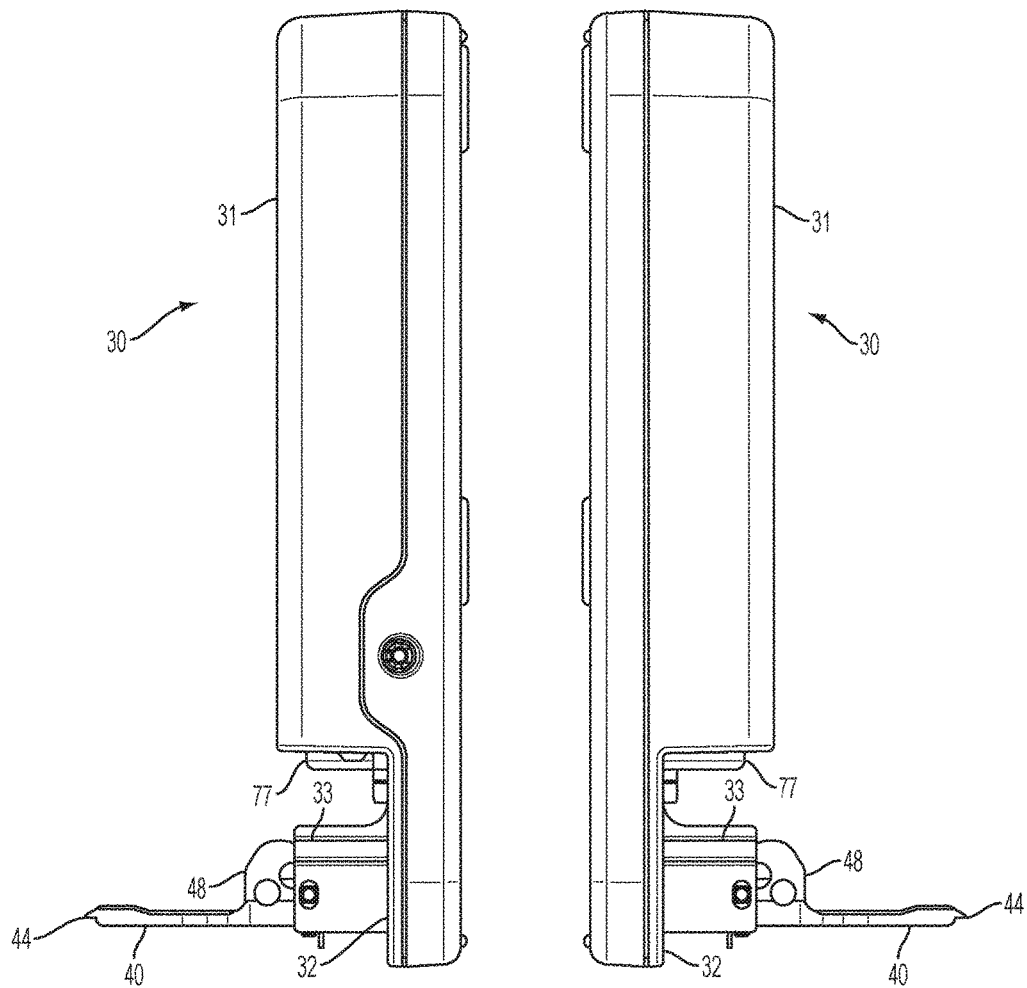
Figure 5F:
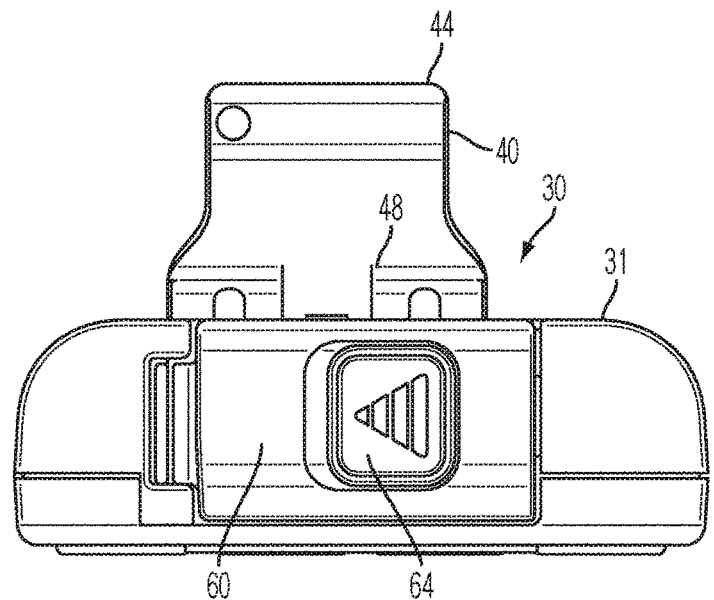
Figure 5G:
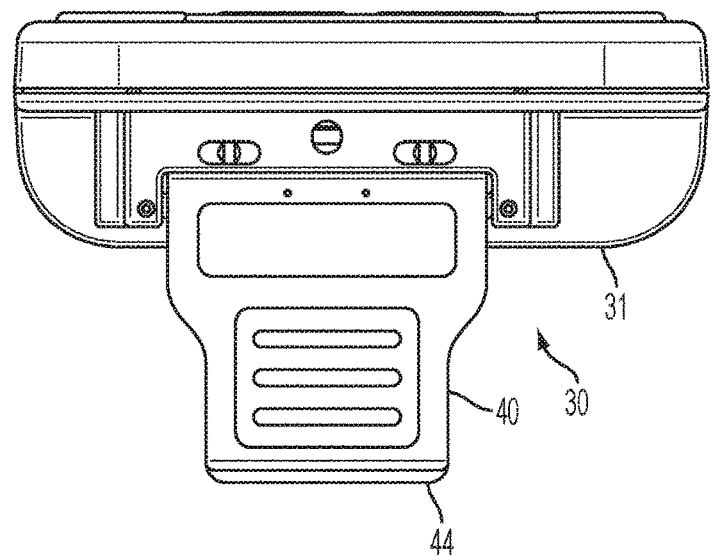
Figure 8B:
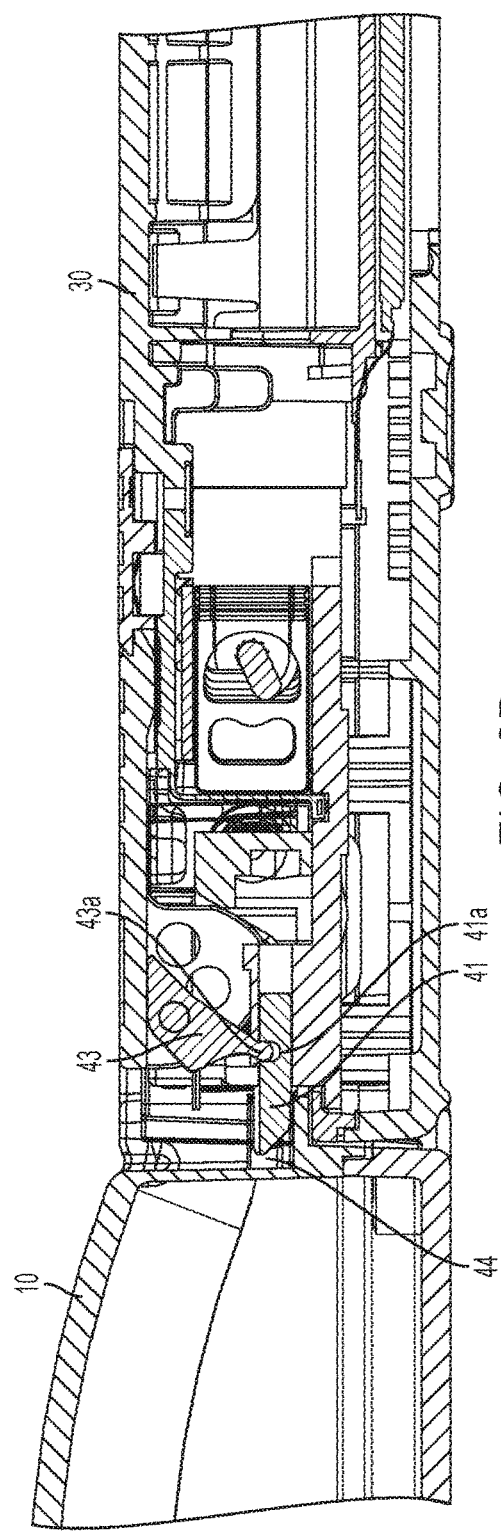
FIG. 8B is a cross-sectional view of the exemplary device taken along line 8B-8B of FIG. 3.
Figure 9B:
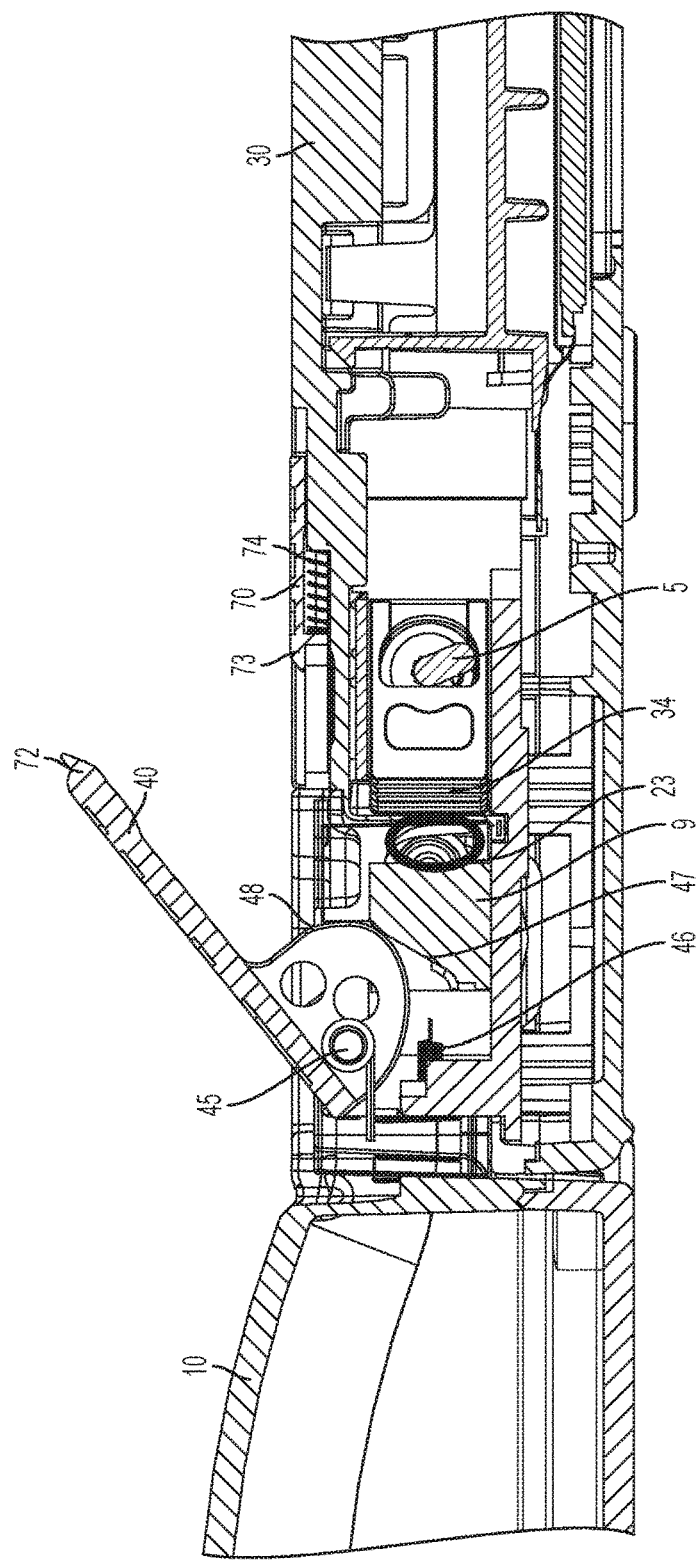
FIG. 9B is a cross-sectional view of the exemplary device of FIG. 9A, with the lock member urged from the open position toward the closed position.

For purpose of illustration and not limitation, as shown for example in FIGS. 5C and 8A-8B, lock member 40 can be biased, such as by a torsion spring 42, to urge lock member 40 toward the open position. Additionally, and embodied herein, lock member 40 can include a pin driver 43, which can have a projection 43a received in notch 41a of alignment pin 41. As embodied herein, pin driver 43 can be urged upon movement of lock member 40 toward the open position to drive the alignment pin 41 away from retention feature 44 in the disposable cassette housing 11 (as shown for example in FIG. 8A). With reference to FIG. 8B, when the lock member 40 is moved to the closed position, the lock member 40 urges the pin driver 43 to drive the alignment pin 41 into the retention feature 44 of the cassette housing 11. For purpose of illustration and not limitation, as embodied herein, the alignment pin 41 can be tapered. The material for the alignment pin 41 can be stainless steel.

Additionally or alternatively, as further embodied herein, cassette 10 can include support rib 54 as shown in FIG. 4B. In this manner, and as embodied herein, pump 30 can include a tubing guide ridge 52 (as shown for example in FIG. 5C), which can engage or restrict movement of the peristaltic tube 23 when the cassette 10 is received within the receiving region 32. When the cassette 10 is received within the receiving region 32, tubing guide ridge 52 can align with support rib 54 (as shown for example in FIG. 4B) on the cassette base region 11, for example and as embodied herein to guide peristaltic tube 23 into engagement with an occlusion sensor (see FIG. 11A). For purpose of illustration, and as embodied herein, support rib 54 can project from boundary 28. Additionally, and as embodied herein, support rib 54 can include a pair of support rib portions. Alternatively, support rib 54 can be configured as a single, unitary rib. As shown in FIG. 4B, for purpose of illustration and not limitation, cassette housing 11 can include a pair of end fittings 24a, 24b to support peristaltic tube 23, and if provided, support rib 54 can be substantially aligned with end fittings 24a, 24b.

Additionally or alternatively, and as further embodied herein, cassette base region 13 can include a contoured surface 80 configured to mate with a corresponding contoured end 81 of pump 30, as shown in FIG. 1. For purpose of illustration, and not limitation, contoured surface 80 can include contoured end portions 80a, 80b having a concave contour relative cassette base region 13 proximate opposing sides of cassette base region 13. Additionally or alternatively, cassette base region 13 can include a selected flat surface 82 proximate an end of cassette housing 11. As embodied herein, flat surface 82 can include flat surface portion 82a, 82b proximate lateral side walls of cassette housing 11. Flat surface 82 of cassette base region 13 can be sized and shaped to engage corresponding flat surface 83 of receiving region 32 of pump 30.

These various features of the cassette base region can be combined in various combinations and arrangements as desired. For example and not limitation, the cassette can be provided with the rails and engagement surface, without an alignment key if desired. Likewise, and without limitation, the cassette can be provided with a pair of alignment keys each offset from the longitudinal axis a.

According to another aspect of the disclosed subject matter, a device for delivering a beneficial agent is provided. The device generally includes a cassette, a pump, a delivery tube and a lock member. The cassette includes a cassette housing with a fluid reservoir defined therein. The cassette housing has a cassette base region. The delivery tube is fluidly coupled with the fluid reservoir. The pump includes a pump housing containing a pump assembly having a fluid drive component. The pump housing has a receiving region to receive the cassette base region. The fluid drive component is disposed proximate the receiving region. The lock member is coupled to the pump housing and is movable between an open position and a closed position. The cassette is capable of being inserted into and removed from the receiving region when the lock member is in the open position. The cassette is secured to the pump with the cassette base region within the receiving region and a length of the delivery tube in operative engagement with the fluid drive component when the lock member is in the closed position.

Additionally, and as embodied herein, an alignment pin can be operatively coupled to the lock member. Movement of the lock member between the open position and the closed position can extend at least a portion of the alignment pin into engagement with the cassette housing. The cassette housing can define a receiving recess proximate the cassette base region to receive the alignment pin when the lock member is moved toward the closed position. The receiving recess can be tapered toward a closed end. For example, the receiving recess can be defined by an alignment key, such as an alignment key, projecting from the cassette body region into the cassette base region. The alignment pin can include a tapered end. To move the alignment pin into an extended position, the lock member can include a protrusion, and the alignment pin can include a notch to receive the protrusion to engage the lock member to operatively couple the alignment pin to the lock member. Furthermore, and as embodied herein, the lock member can include a latch, and receiving region can further include a torsion spring mechanically coupled to the lock member to urge the latch toward the open position.

In addition, and as embodied herein, the latch can further include a latch cam surface, and the pump can further include an occlusion block disposed proximate the receiving region and having an occlusion block cam surface. The occlusion block can be biased to urge the occlusion block cam surface against the latch cam surface. The latch cam surface and the occlusion block cam surface thus can be configured to urge the occlusion block toward an operative position to hold the peristaltic tube in functional relationship to the fluid drive component when the latch is moved from the open position toward the closed position. The latch cam surface and the occlusion block cam surface can be configured to define a dead zone where the occlusion block remains in the operative position during continued movement of the latch continues from the open position to the closed position. The dead zone can be defined by 10 degrees of final movement of the latch from the open position to the closed position. The latch comprises a pivotal latch mounted on a hinge. Alternatively, the latch can include a draw latch mounted for sliding movement. The features of this aspect can be combined with one or more feature of the apparatus and methods set forth above.

With reference to FIG. 6, the pump housing 31 can include a pump assembly 200 having a fluid drive component. The pump assembly 200 can be configured, for example, as a peristaltic pump. For example, a peristaltic pump can include a motor 3, a cam shaft 2, and a plurality of finger plates 34 disposed along the length of the cam shaft 2. The cam shaft 2 is coupled to the motor 3 for rotation about a longitudinal axis a of the cam shaft 2, and has at least one radially-outward projection 5 defining a helical engagement portion disposed along a length of the cam shaft 2. The plurality of finger plates 34 are disposed along the length of the cam shaft 2. Each finger plate 34 is mounted for movement in a transverse direction relative to the longitudinal axis a of the cam shaft 2, and has an aperture defined therein to receive the cam shaft 2 therethrough. Additional details of suitable fluid drive components and related features of the pump suitable for use herewith are described in U.S. patent application Ser. No. 14/586,923, filed Dec. 30, 2014; Ser. No. 14/586,930, filed Dec. 30, 2014; each of which is incorporated by reference in its entirety.

Figure 7F:
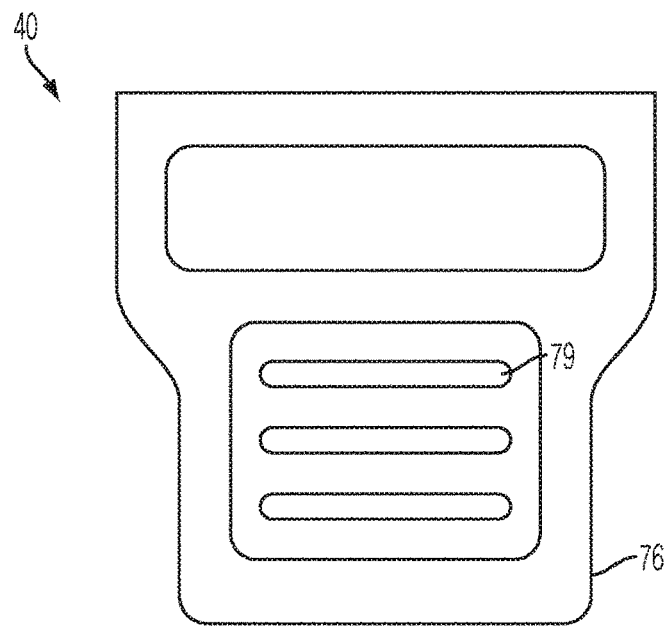
FIG. 7F is a top view of the exemplary lock member of FIG. 7A.
Figure 7G:
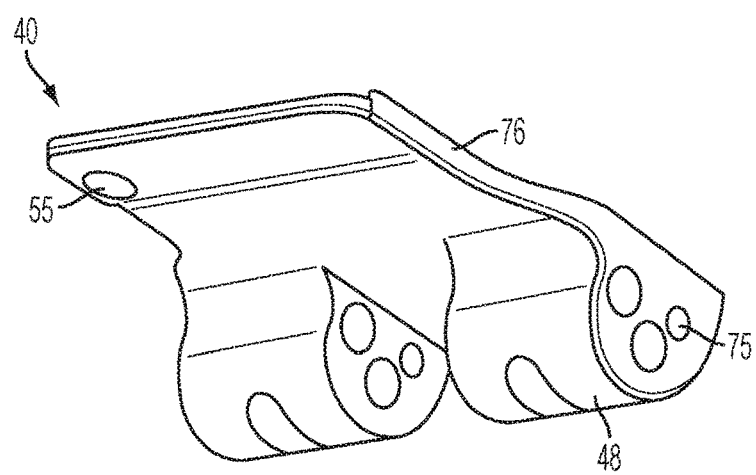
FIG. 7G is a bottom perspective view of the exemplary lock member of FIG. 7A.

For purpose of illustration and not limitation, as embodied herein, lock member 40 can be configured as a latch or cam lever, such as a pivotal latch, a draw latch, or any other suitable latching mechanism. As shown for example in FIGS. 6 and 7A-7G, lock member 40 can be configured as a pivotal latch. Lock member 40 can include a latch cam surface 48 to engage an occlusion block, as discussed further herein. Additionally, and as embodied herein, lock member 40 can include a hinge receptacle 75 to receive a hinge pin 45 to allow pivotal movement of lock member 40. As embodied herein, hinge pin 45 can also engage pin driver 43 to lock member 40 to allow pivotal movement of pin driver 43 with lock member 40, as discussed further herein. Additionally, lock member 40 can be biased toward an open position, such as by torsion spring 42. Furthermore, and as embodied herein, lock member 40 can include a closure sensor receptacle 55 to receive a closure sensor, such as for purpose of illustration and not limitation, as embodied herein, a magnet to trigger a reed sensor, as discussed further herein. As shown in FIG. 7A, and as embodied herein, lock member 40 includes a tapered end 76 sized and shaped to engage a corresponding recess in cassette base region 13, as discussed further herein. As shown in FIG. 7F, for purpose of illustration and not limitation, lock member 40 can include one or more raised surface features 79 to assist with engagement of lock member 40, for example by a user, to move lock member 40 between the open position and closed position.

Referring now to FIGS. 9A-9D, when the lock member 40 is moved into the closed position, the lock member 40, urged by torsion spring 42, pivots about the lever hinge 45. Tension springs 46 urge the occlusion block cam surface 47 of occlusion block 9 against the latch cam surface 48 of lock member 40. As such, and with reference to FIGS. 9A-9D, the occlusion block 9 can be positioned, by the stroke of the lock member 40, an appropriate distance to dispose the peristaltic tube 23 operatively against the peristaltic fingers 34 when closed, as shown for example in FIG. 9D.

As illustrated for example in FIG. 9C, with the lock member 40 within a certain angle of rotation α, for example and without limitation, within a range of approximately 0°-10° relative to the pump 30, the lock member lever cam surface 48 as embodied herein enters a so-called "dead zone." That is, within the "dead zone," the lock member 40 can continue to be closed and latch against the pump housing 31, while the occlusion block 9 remains positioned in a fully latched state. In this manner, the occlusion block 9 is properly positioned relative to the peristaltic fingers 34 even if the lock member 40 is not fully closed, and thus the effect of mechanical tolerances in the locking assembly on the position of the occlusion block 9 can be reduced. A closure indicator, embodied herein as a magnet disposed in closure sensor receptacle 55 of lock member 40, or other suitable closure elements, can be detected by a closure sensor, embodied herein as a magnetic field detector disposed in the pump housing 31 proximate the lock member 40 to allow the pump assembly to detect when the lock member 40 is fully closed.

As illustrated for example in FIG. 9D, with lock member 40 further urged into the closed position, distal projection 72 of lock member 40 moves along cam surface of lock member release 70 to urge lock member release 70 away from lock member 40 and allow distal projection 72 to move beyond and engage corresponding projection 73 of release 70. In this manner, lock member 40 is secured in the closed position by projection 73 of release 70, which is biased into engagement with lock member 40 by spring 74. To release lock member 40, lock member release 70 can be urged away from lock member 40 to move projection 73 out of alignment with distal projection 72 to allow lock member 40, which as described herein can be biased in the open position, to be urged into the open position, as embodied herein by torsion spring 42.

As illustrated for example in FIG. 6, in some embodiments, set screws 49 can be provided to the lever hinge pin 45 to allow for adjustment during assembly to account for mechanical tolerances and provide a suitable occlusion distance. Polishing the surface of lock member 40 can reduce friction between the occlusion block surface 47 and the lock member 40. The roughness average of the cam lever can be about 0.4 μm. This can be accomplished by one or more of tumbling, anodizing, and polishing the lock member 40. Additionally, providing an occlusion block cam surface 47 with a slope of 30 degrees can increase the vertical component of the force of the lock member 40.

According to another aspect of the disclosed subject matter, and further to the above a device for delivering a beneficial agent is provided. The device generally includes a cassette, a pump, a delivery tube and a lock member. The cassette includes a cassette housing with a fluid reservoir defined therein. The cassette housing has a cassette base region, and the cassette base region includes a radio frequency identification (RFID) shell housing a RFID tag. The delivery tube is fluidly coupled with the fluid reservoir. The pump includes a pump housing containing a RFID reader and a pump assembly having a fluid drive component. The pump housing has a receiving region to receive the cassette base region. The RFID reader and the fluid drive component are disposed proximate the receiving region. The lock member is coupled to the pump housing and is movable between an open position and a closed position. The cassette is capable of being inserted into and removed from the receiving region when the lock member is in the open position. The cassette is secured to the pump with the cassette base region within the receiving region with the RFID tag disposed proximate the RFID reader and a length of the delivery tube in operative engagement with the fluid drive component when the lock member is in the closed position.

Additionally, and as embodied herein, the RFID shell can include a raised surface relative an adjacent surface of the cassette base region. The raised surface can have a height of about 2 mm relative the adjacent surface. The receiving region can include a dimple having a bottom radius of 2.5 mm and a top radius of 6.25 mm, each as measured from an exterior of the pump housing. The RFID tag can be molded in the RFID shell. Additionally or alternatively, the RFID tag can be bonded to the RFID shell. The RFID tag can include identification information for the cassette encoded thereon. The RFID tag can include attribute information of a beneficial agent contained in the fluid reservoir encoded thereon. The attribute information can include one or more of a concentration, a formation date, and an expiration date of the beneficial agent.

Furthermore, and as embodied herein, the receiving region can further include a RFID receiving region with the RFID reader housed therein. The RFID receiving region can be configured to engage the RFID shell when the cassette is secured to the pump with the cassette base region within the receiving region of the pump housing. The RFID receiving region can have a shape configured to mate with the RFID shell. For example, the RFID shell can include a raised surface relative an adjacent surface of the cassette base region, and the RFID receiving region can include a dimple configured to receive the raised surface when the cassette is secured to the pump with the cassette base region within the receiving region of the pump housing. The RFID shell and RFID receiving region can be configured to dispose the RFID tag within about 5 mm of the RFID reader when the cassette is secured to the pump with the cassette base region within the receiving region of the pump housing. The RFID reader can have a range of detection configured to read the RFID tag only when the RFID receiving region is in engagement with the RFID shell. The device can further include a processor coupled to the RFID reader and configured to verify identification information for the cassette encoded on the RFID tag. Additionally or alternatively, the processor can be coupled to the RFID reader and configured to enable operation of the pump if an expiration date of the beneficial agent encoded on the RFID tag is not exceeded. In addition or as a further alternative, the processor can be coupled to the RFID reader and configured to determine one or more dosing options based at least in part on a concentration of the beneficial agent encoded on the RFID tag. The RFID tag can include high or ultra-high radio frequency ID.

According to another aspect of the disclosed subject matter, and further to the above, a drug delivery reservoir cassette for a pump having an RFID reader, a receiving region configured to receive the cassette, and a lock member movable between an open position and a closed position is provided. The cassette includes a cassette housing with a fluid reservoir defined therein. The cassette housing has a cassette base region. The cassette base region includes a radio frequency identification (RFID) shell housing a RFID tag configured to be read by the RFID reader. The cassette is capable of being inserted into and removed from the receiving region when the lock member is in the open position, and the cassette is secured to the pump with the cassette base region within the receiving region with the RFID tag disposed proximate the RFID reader when the lock member is in the closed position.

The cassette can include any combination of features described herein. For example, and as embodied herein, the RFID shell comprises a raised surface relative an adjacent surface of the cassette base region. the RFID shell can include a raised surface relative an adjacent surface of the cassette base region. The raised surface can have a height of about 2 mm relative the adjacent surface. The receiving region can include a dimple having a bottom radius of 2.5 mm and a top radius of 6.25 mm, each as measured from an exterior of the pump housing. The RFID tag can be molded in the RFID shell. Additionally or alternatively, the RFID tag can be bonded to the RFID shell. The RFID tag can include identification information for the cassette encoded thereon. The RFID tag can include attribute information of a beneficial agent contained in the fluid reservoir encoded thereon. The attribute information can include one or more of a concentration, a formation date, and an expiration date of the beneficial agent. The features of these aspects can be combined with one or more features of the apparatus and methods set forth above.

Figure 10:
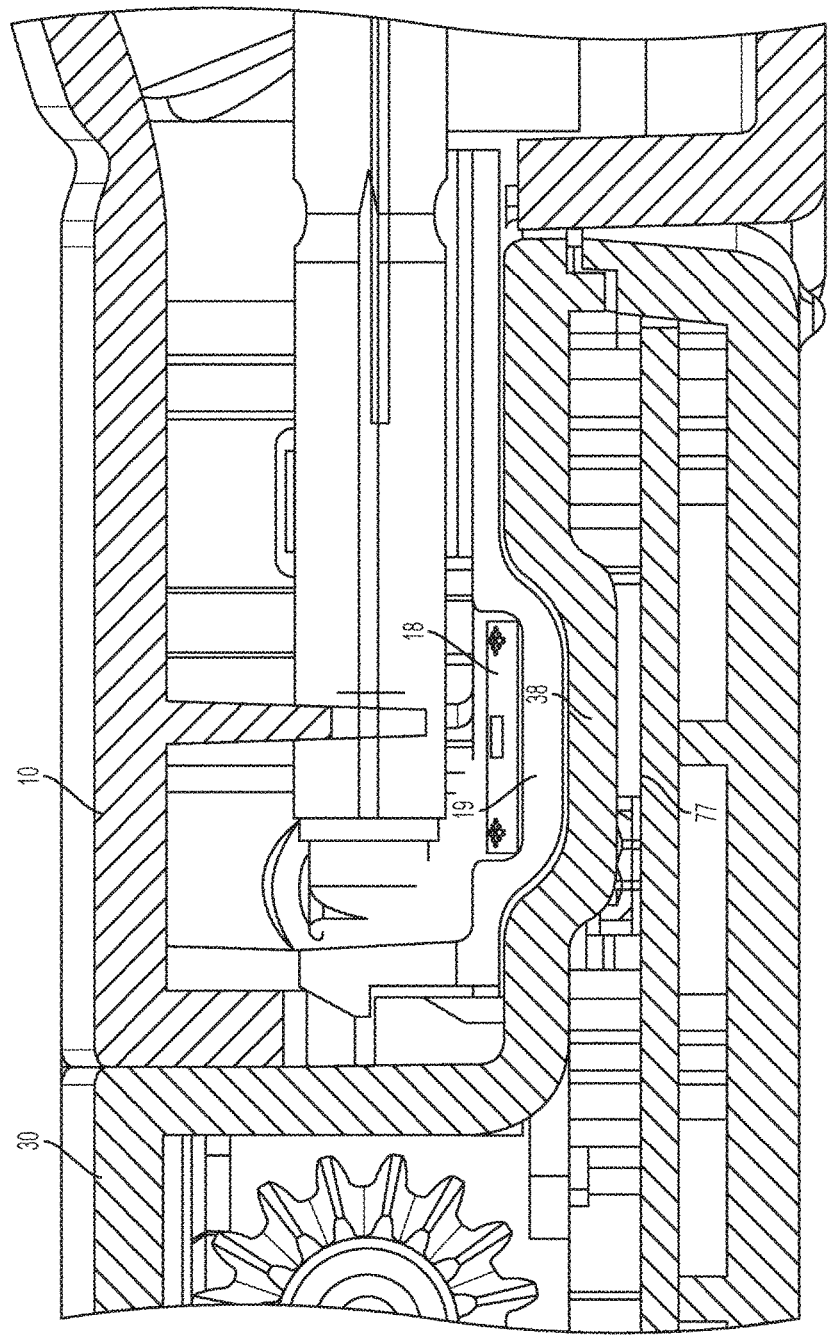
FIG. 10 is a cross-sectional view of the exemplary device taken along line 10-10 of FIG. 3.

For example and as embodied herein, cassette 10 can include an RFID enclosure shell to house an RFID tag. RFID enclosure shell can be configured to engage RFID tag with a corresponding RFID reader in pump 30. With reference to FIGS. 4B and 10, for purpose of illustration and not limitation, the RFID enclosure shell 19 can be shaped as a raised surface projecting into cassette base region 13. As shown for example in FIG. 10, RFID tag 18 may be disposed within RFID enclosure shell 19 by any suitable technique. For example and without limitation, RFID tag 18 can be injection molded into the RFID enclosure shell 19. Alternatively, the RFID tag 18 can be bonded to the RFID enclosure shell 19, for example by a potting technique, such as epoxy potting.

Referring now to FIGS. 5C and 10, as embodied herein, the pump housing 31 can have a RFID receiving region 38 to house an RFID reader 77 and can engage with the RFID enclosure shell 19 of the cassette housing 11. The RFID receiving region 38 can be configured as a dimple disposed in the receiving region 32 of the pump housing 31. For example, and as embodied herein, the dimple can be 1.9 mm deep, and can include a 2.5 mm bottom radius and a 6.25 mm top radius measured from the exterior of the pump housing 31. The RFID enclosure shell 19 and the RFID receiving region 38 can be configured to allow the RFID tag 18 to be disposed within 5 mm of an RFID reader 77 when the cassette housing 11 and the pump housing 31 are joined together, as described in further detail below. For purpose of illustration, and not limitation, as embodied herein, RFID reader 77 can be embedded in a circuit board disposed in pump housing 31. RFID reader 77 can be "box-shaped,"

such as a square or rectangular spiral, and formed by a number of wire windings, embodied herein as 14 coil windings, with 7 windings in each of two layers of the PCB. As such, RFID reader 77 can have outer cross-dimensions of 0.360"×0.372" and can have a central aperture having inner cross-dimensions of 0.204"×0.228". In this manner, RFID reader 77 can be configured with a range of detection to only detect RFID tag 18 when the cassette housing 11 is joined to the pump housing 31, such that another RFID tag further away from the RFID reader 77 would be outside the range of detection. Additionally or alternatively, the RFID reader 77 can be configured to determine which one of a plurality of RFID tags is closer to the RFID reader 77, and thus can determine which one of a plurality of cassette housings is joined to the pump housing 31. RFID reader 77 can utilize any suitable RFID techniques, including and without limitation, low, high, or ultra-high radio frequency ID.

RFID reader 77 also can be configured to identify drug cassettes and read information encoded in RFID tag 18. In this manner, the system can be used to detect cassettes that are not compatible or warrantied for use with the pump or otherwise to deter counterfeiting of drug cassettes. For purpose of illustration and not limitation, RFID tag 18 can include identification information for cassette 10 encoded thereon. Additionally or alternatively, RFID tag 18 can include attribute information of a beneficial agent contained in the fluid reservoir encoded thereon, which can include, without limitation, a concentration, a formation date, and/or an expiration date of the beneficial agent. RFID reader 77 can be coupled to a processor, which can be configured to receive and verify the identification information for cassette 10 encoded on the RFID tag, and can be further configured to enable operation of pump 30 only if the identification information for cassette 10 can be verified. Additionally or alternatively, the processor can be configured to enable operation of pump 30 only if an expiration date of the beneficial agent, if encoded on the RFID tag 18, is not exceeded. Additionally or as a further alternative, processor coupled to RFID reader 77 can be configured to determine one or more dosing options based at least in part on a concentration of the beneficial agent contained within cassette 10, if encoded on the RFID tag 18.

The housing provided herein can be made of a variety of constructions and configurations. For example, and not limitation, with reference to FIGS. 1-3 and 5C, the pump housing 31 can include a rear closure portion 35 and a front closure portion 36. One of the closure portions, such as the rear closure portion 35 as embodied herein, can include a membrane 37 disposed between the receiving region 32 and the fluid drive component, as embodied herein, to cover the finger plates of the peristaltic pump. In such a configuration, the finger plates of the peristaltic pump will push on the peristaltic tube 23 with the membrane 37 disposed in-between the fingers and the peristaltic tube 23. The membrane 37 can prevent debris and fluid from contacting and interfering with the pumping mechanism. The membrane 37 can be a thermoformed or injection molded membrane, which can be over-molded onto the rear closure portion 35. As embodied herein, the membrane 37 can define a rectangular-shaped protrusion extending from an end of the rear closure portion 35. Membrane 37 can define vertical sides extending from the rear closure portion 35 and forming slightly rounded corners at an outer face of the membrane 37. Additionally or alternatively, membrane 37 can have a first side extending from the rear closure portion 35 to the outer face of the membrane 37 at a gradual slope, and can have an opposing side extending vertically from the rear closure portion 35 and forming rounded corners proximate the outer face of the membrane 37. In this manner, the gradual slope formed proximate the inlet side of the peristaltic tube 23 can allow for a more gradual compression of the peristaltic tube 23.

Furthermore, and as embodied herein, the membrane 37 can be formed having dimensions and using materials to reduce rigidity, and thus utilize less force from the pump to move the membrane 37 and engage the peristaltic tube 23. For example, increased thickness of the membrane 37 can cause increased force applied by the pump during operation, and thus, increased power utilized and decreased battery performance. As such, the membrane 37 can have a thickness between 0.009 inches and 0.019 inches, and in some embodiments can have a thickness between 0.009 inches and 0.015 inches, which can provide suitable protection from debris and fluid ingress with suitable battery consumption. The material properties of the membrane 37, including flexibility, can similarly affect battery performance. In some embodiments, the membrane can be formed from Elastollan C80A, Estane 2103-90A, Elastollan S85A, Elastollan S95A or other suitable materials.

Figure 11A:
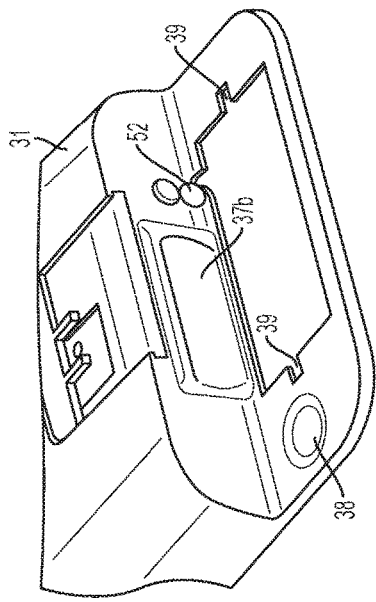
FIG. 11A is an enlarged perspective view of an alternative embodiment of a membrane for a pump housing in accordance with the disclosed subject matter.
Figure 11B:
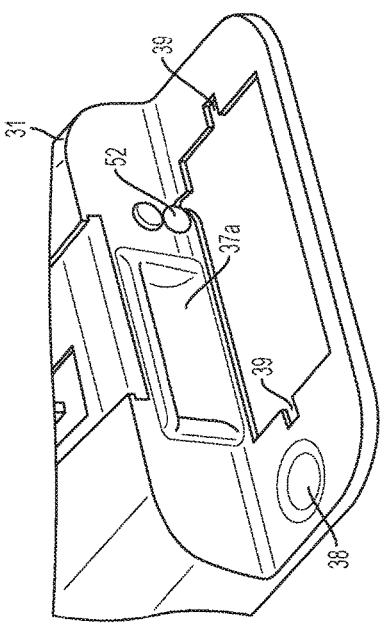
FIG. 11B is an enlarged perspective view of another alternative embodiment of a membrane for a pump housing in accordance with the disclosed subject matter.
Figure 11C:
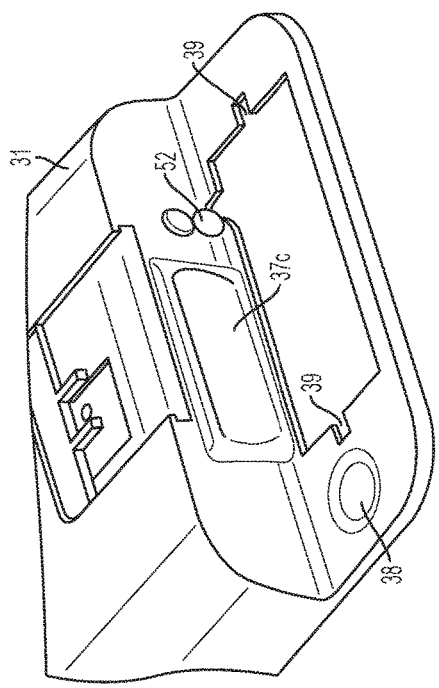
FIG. 11C is an enlarged perspective view of yet another alternative embodiment of a membrane for a pump housing in accordance with the disclosed subject matter.

Referring now to FIGS. 11A-11C, alternative embodiments of a membrane 37 are illustrated. As shown for example in FIG. 11A, membrane 37a can include rounded corners on each end of membrane 37a, and each rounded corner can be tapered inward toward a center of membrane 37a. Alternatively, as shown for example in FIG. 11B, membrane 37b can include rounded corners on each end of membrane 37b, and each rounded corner can be tapered outward away from a center of membrane 37b. As a further alternative, as shown for example in FIG. 11C, membrane 37c can include rounded corners on each end of membrane 37c, one of the rounded corners being tapered inward toward a center of membrane 37c and one of the rounded corners being tapered outward away from a center of membrane 37c. In each configuration, the curvature formed proximate the inlet side and outlet side of the peristaltic tube 23 can allow for peristaltic tube 23 to expand more easily after compression. For example and without limitation, as embodied herein, the curvature proximate the inlet side can reduce or prevent contact with one or more end fittings or joints proximate inlet side of peristaltic tube 23. Additionally or alternatively, the curvature formed proximate the outlet side can prevent or inhibit the membrane from being urged away from the occlusion sensor. Membrane 37, 37a, 37b and 37c can be formed having any suitable thickness to prevent debris or liquid from entering pump housing 31 and to avoid interference with peristaltic tube 23 and/or engagement of finger plates 4 therewith. For purpose of illustration and not limitation, as embodied herein, membrane 37, 37a, 37b and 37c can have a thickness of 0.33 mm.

For purpose of illustration and not limitation, as embodied herein, membrane 37 can be configured to reduce or prevent membrane tenting, which can cause the membrane to exert undesired pressure on peristaltic tube. Such pressure can inhibit or prevent the peristaltic tube 23 from fully opening and thus can cause efficiency loss in the flow rate of material through the peristaltic tube. With reference to FIGS. 11F and 11G, a top and side view, respectively, of a membrane 37, peristaltic tube 23 and finger plates 34. As shown in FIG. 11F, the finger plates 34 can be disposed along the length of the cam shaft 2. As the cam shaft 2 rotates, one or more of the finger plates 34 is mounted for movement in a transverse direction relative to the longitudinal axis of the cam shaft 2, and the finger plates 34 can protrude from the slot to engage an interior surface of the membrane 37. When the cassette base region is in the receiving region 32 of pump housing, and the cassette is secured to the pump in a closed position (see, e.g., FIG. 9D), the finger plates 34 further engage the peristaltic pump to deliver materials or agents through the pump. During the pumping motion of the fluid drive component, the finger plates 34 can be oriented to engage the peristaltic pump 23 at both the inlet side 106 and outlet side 107. Membrane tenting can urge a flat membrane 37 against the peristaltic tube 23 and exert force 103 on the peristaltic pump along the length 104 and width 105 of the pump. As such, peristaltic tube 23 can remain fully or partially closed, which can obstruct flow through peristaltic tube 23. Membrane 37 can thus be configured to have suitable any length, width, shape, thickness, or material to avoid membrane tenting. Membrane 37 can also be configured to minimize debris from interfering with the fluid drive component or other components of the pump assembly. Membrane 37 can further be joined with the pump housing in different configurations to achieve these and other advantages as described herein. For purpose of illustration and without limitation, membrane 37 can be curved, supported, lengthened, or otherwise shaped to conform to the shape that can form when both inlet 106 and outlet 107 of the peristaltic pump are compressed by finger plates 34. For example, and without limitation, membrane 37 can thus have a trapezoidal shape, but other shapes are possible depending on the configuration of the pump mechanism.

Figure 11D:
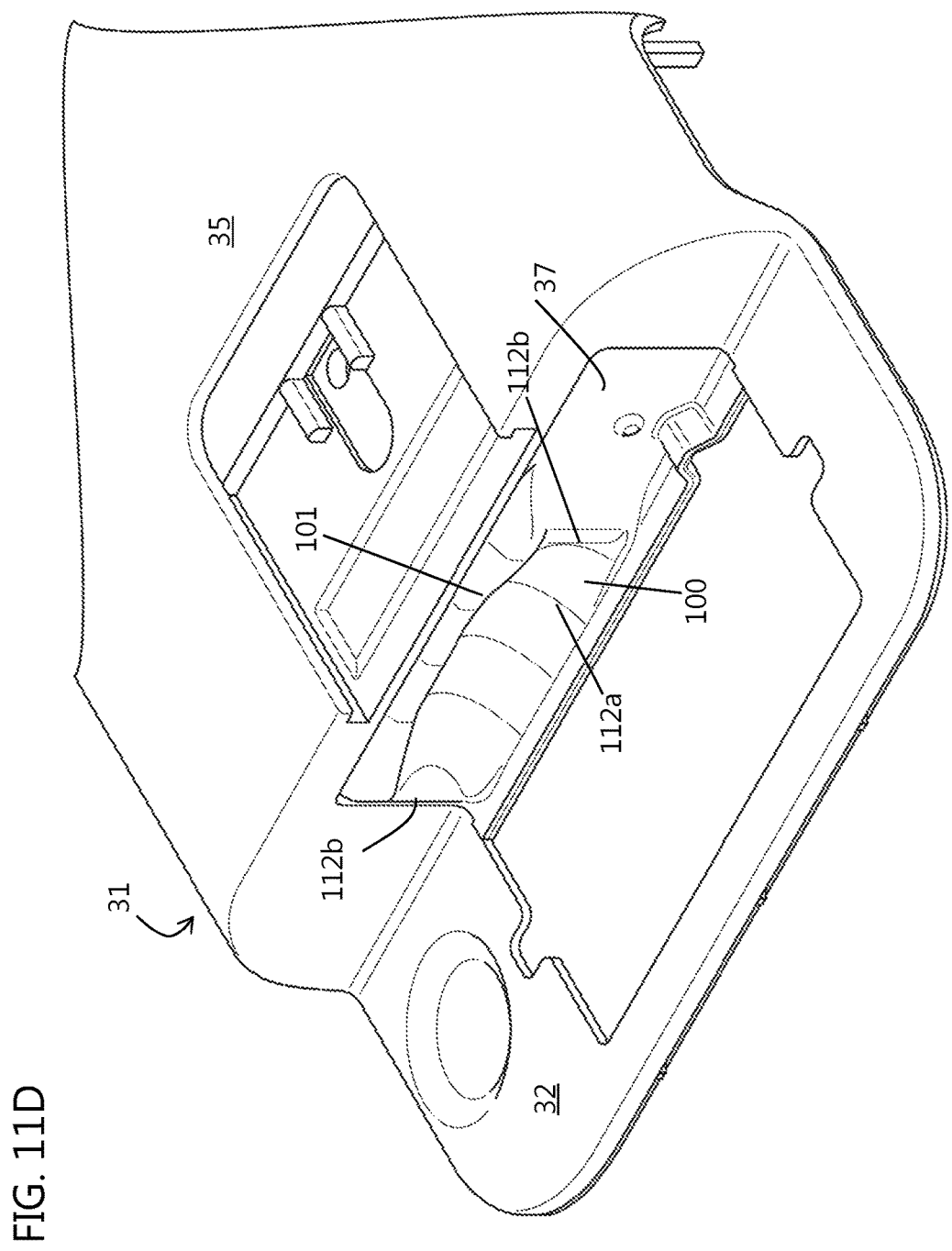
FIG. 11D is a top perspective view of an exemplary embodiment of a membrane for a pump housing in accordance with the disclosed subject matter.
Figure 11E:
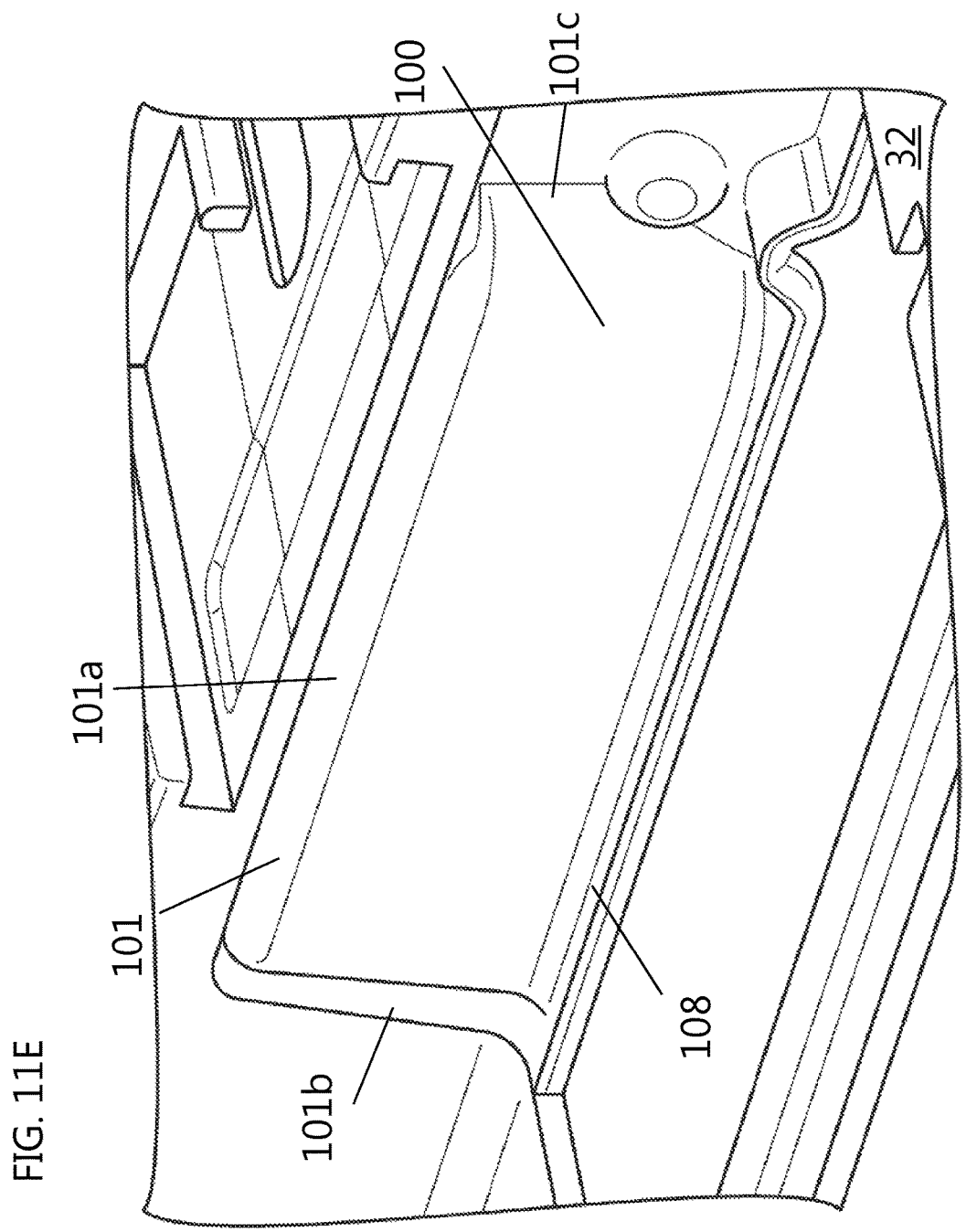
FIG. 11E is an enlarged perspective view of a pump housing including a slot for a membrane, in accordance with the disclosed subject matter.

Referring now to FIGS. 11D and 11E, alternative embodiments of membrane 37 and rear closure portion 35 of the pump housing 31 are illustrated. Membrane 37 may be configured to have any length, width, thickness, or material to cover a slot 100 formed in the rear closure portion 35. The slot 100 can receive a plurality of finger plates 34 of a fluid drive component within pump housing 31. The finger plates 34 can protrude through the slot to engage an interior surface of the membrane 37 and a peristaltic tube 23 when the cassette base region is received by the receiving region 32. For purpose of illustration and not limitation, rounded corners and an overall rounded shape of membrane 37 can be supported by one or more edges 101 framing a slot 100 in the rear closure portion 35, and rounded corners and an overall rounded shape of membrane 37 can result. The slot 100 can be proximate to a lateral boundary 102 (this is not shown) of the receiving region 32. The one or more edges 101 may protrude from the pump housing 31, which can be sized and shaped to support the membrane 37. As such, membrane 37 can be molded or shaped over the edges 101. For the purpose of illustration not limitation, slot 100 can have a rectangular shape and can include, for example, a lateral edge 101a and opposing end edges 101b and 101c to support membrane 37. As embodied herein, membrane 37 can be adhered to an edge between the receiving region 32 and rear closure portion 35 in any suitable manner, such as using glue. Additionally or alternatively, membrane 37 can be partially over-molded onto the receiving region 32. The receiving region can include a support rib 108 proximate the rear closure portion to further support membrane 37.

With reference to FIG. 11D, membrane 37 can be lengthened or shaped to have a curvature corresponding to a curvature 112a of the peristaltic tube, which can reduce or prevent membrane tenting. Additionally or alternatively, and as embodied herein, membrane 37 can include a curvature 112b proximate the inlet end 106 and/or the outlet end 107 corresponding to a position of the finger plates 34 when the peristaltic tube is engaged by the finger plates at the inlet end 106 and the outlet end 107. In this manner, when the finger plates engage the peristaltic tube at both the inlet end 106 and the outlet end 107, the shape of the membrane can resist flattening of the membrane, which can cause the membrane to apply a force against the peristaltic tube.

Reference is now made to FIGS. 11H and 11I, which respectively illustrate top and side views of the membrane 37 of FIGS. 11F and 11G, each of which includes additional or alternative shapes as described further below. As shown for example in FIG. 11H, membrane 37d can include more material along its length compared to membrane 37, which can extend along a longitudinal axis of the peristaltic tube 23. For example and as embodied herein, membrane 37d can also include inlet curvature 109a and outlet curvature 109b. Inlet curvature 109a and outlet curvature 109b may be formed proximate to the inlet 106 and outlet 107 ends of peristaltic tube 23, and can also be convex toward the peristaltic tube 23 so that when finger plates 34 engage the membrane 37d and the peristaltic tube 23 at the respective inlet 106 or outlet 107, the convex curvature allows more stretching of the membrane 37d proximate the inlet and outlet locations. This can avoid stretching of membrane 37 along the length of membrane 37d and thus avoid membrane tenting. For example and without limitation, membrane 37d can have a radius of curvature of between 20-30 mm along the length of the peristaltic tube 23 at inlet curvature 109a and outlet curvature 109b, and as embodied herein, can have a radius of curvature of 25 mm along the length of the peristaltic tube 23, as shown in FIG. 11H. As further shown for example in FIG. 11I, membrane 37 can also include more material along the width of membrane 37d compared to membrane 37, which can extend along a radial axis of the peristaltic tube 23. Membrane 37d can also have a curvature 109c corresponding more closely to a curvature of the peristaltic tube 23. For example and without limitation, membrane 37d can have a radius of curvature of between 6-8 mm along the curvature of the peristaltic tube 23 as shown in, and as embodied herein, can have a radius of curvature of 7 mm along the curvature of the peristaltic tube 23, as shown in FIG. 11I. Other curvatures may also be possible.

Figure 11K:
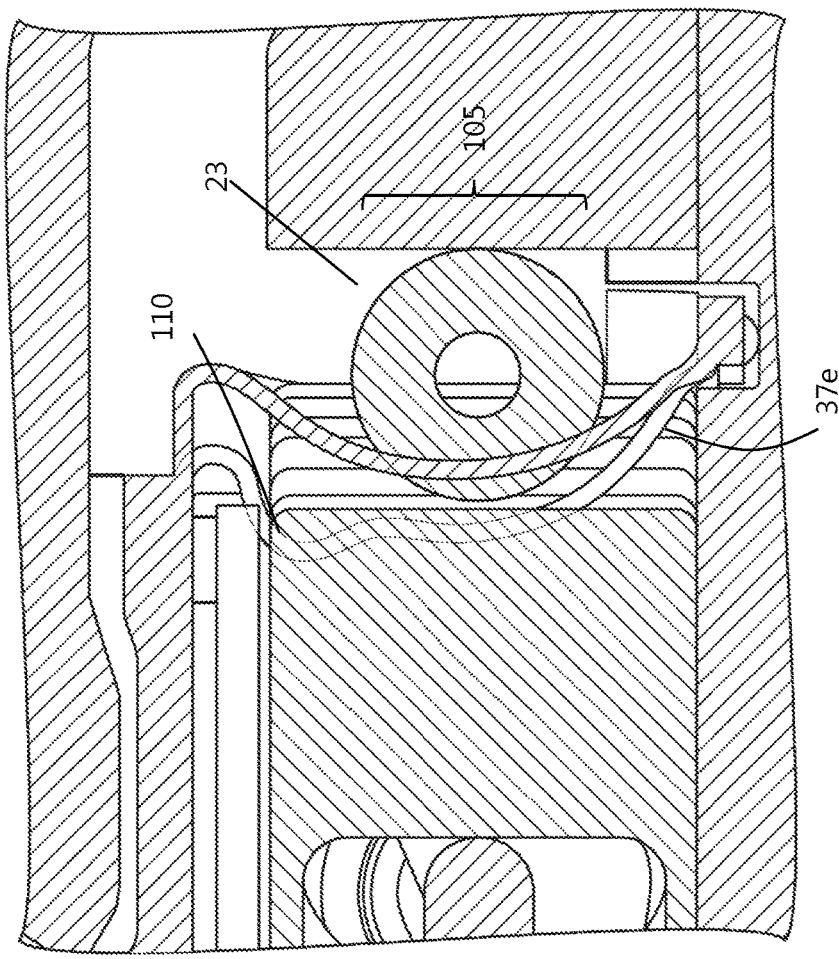
FIGS. 11J and 11K are top and side views, respectively, of another alternative embodiment of the membrane of FIGS. 11F and 11G in accordance with the disclosed subject matter.
Figure 11J:
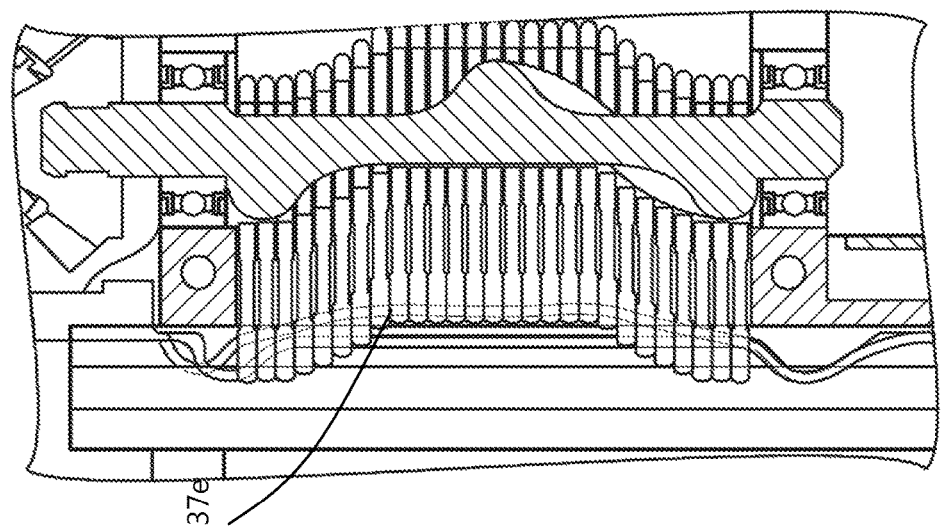
Figure 11M:
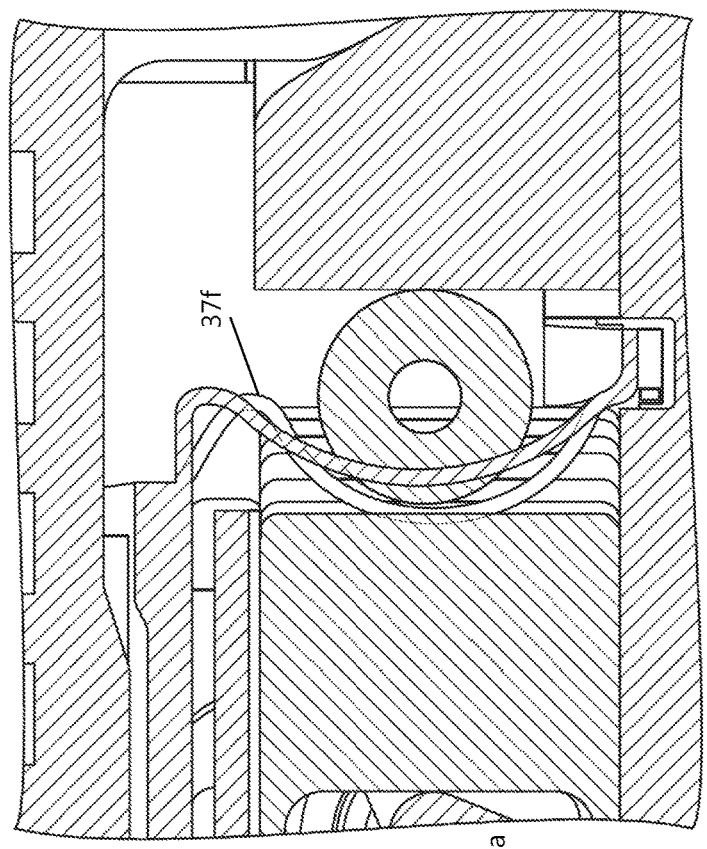
FIGS. 11L and 11M are top and side views, respectively, of yet another alternative embodiment of the membrane of FIGS. 11F and 11G in accordance with the disclosed subject matter.
Figure 11L:
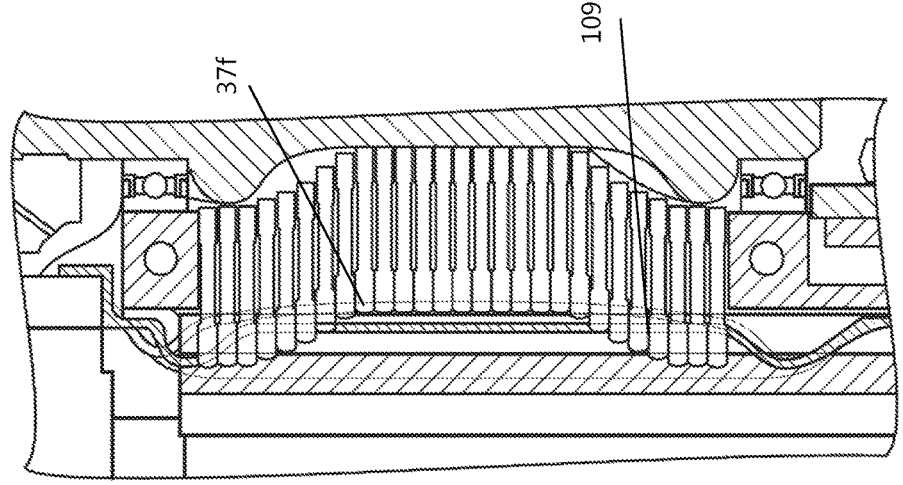
Figure 11O:
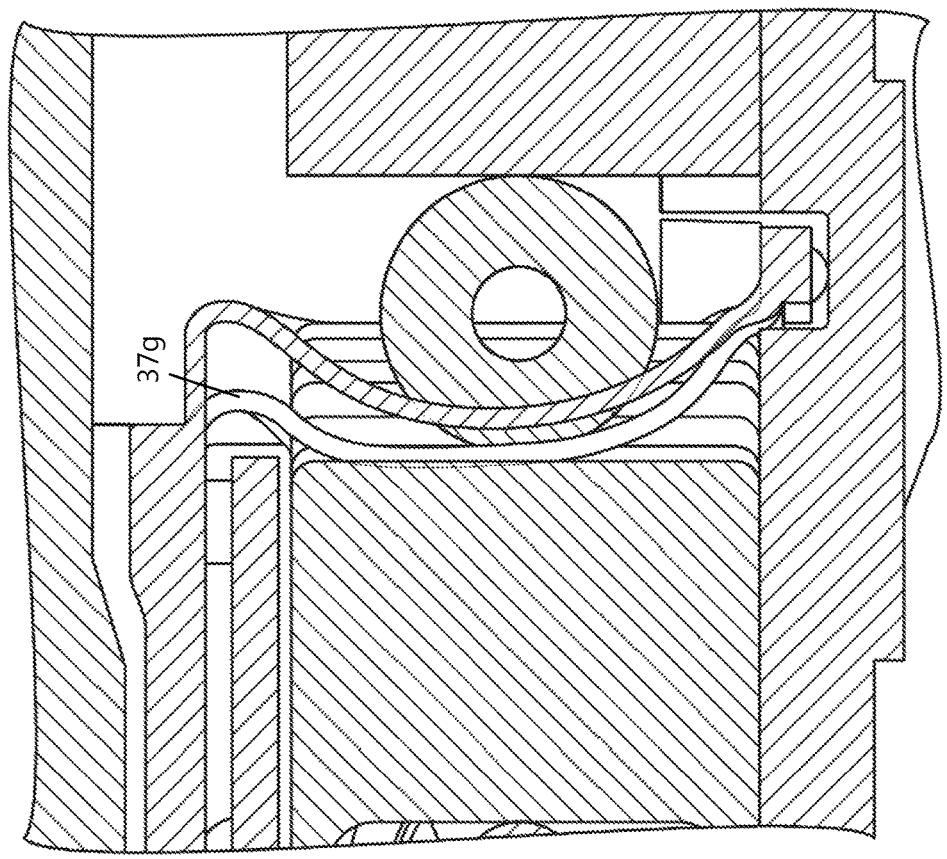
FIGS. 11N and 11O are top and side views, respectively, of yet another alternative embodiment of the membrane of FIGS. 11F and 11G in accordance with the disclosed subject matter.
Figure 11N:
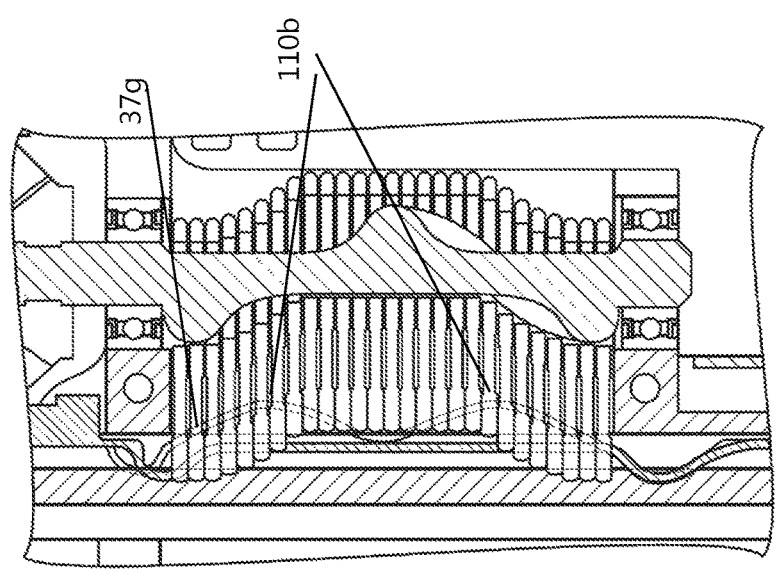
Figure 11Q:
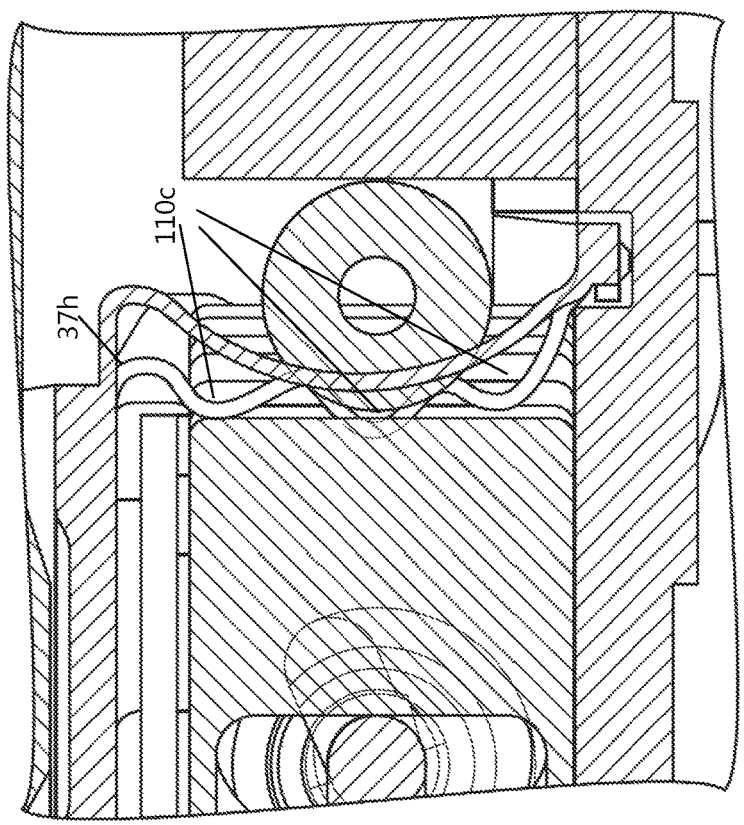
FIGS. 11P and 11Q are top and side views, respectively, of yet another alternative embodiment of the membrane of FIGS. 11F and 11G in accordance with the disclosed subject matter.
Figure 11P:
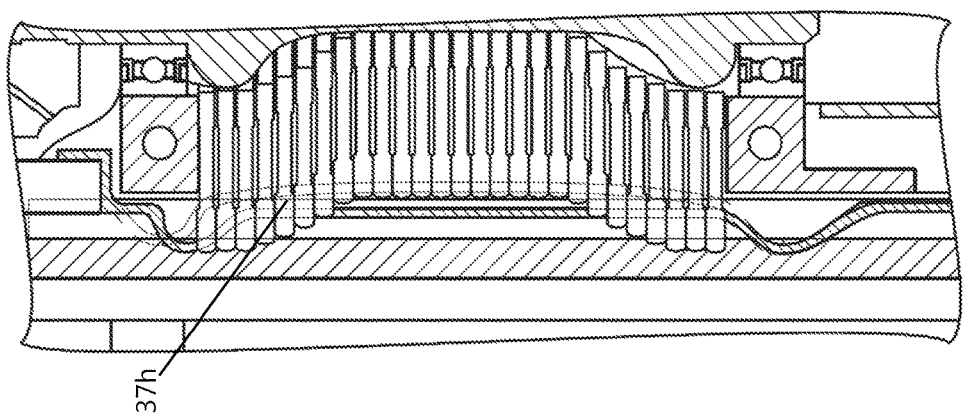

Referring to FIG. 11K, for example and without limitation, membrane 37e can include one or more bellows 110 to allow extension of the membrane 37e. For example, as shown in FIG. 11K, the bellow 110 allows extension of the membrane 37e along the width 105 dimension of tube 23.

For the purpose of understanding and not limitation, Tables 1-3 are provided to illustrate various operational characteristics achieved by different membrane configurations disclosed herein. Table 1, for example, illustrates the average flow rate of material within a peristaltic tube given different characteristics of membrane 37, including curvature and glue support or rib support. In one example, reliability was improved with higher durometer materials and better flow rate performance with lower durometer materials. Membrane 37 can be formed from any suitable material. For example, and as embodied herein, Elastollan S95A55N can be used to achieve desired performance. For example, Elastollan S95A55N can provide suitable flow rate efficiency due at least in part to a relatively higher durometer. Selecting a suitable thickness and shape of the membrane can further improve the flow rate efficiency as described herein. For purpose of understanding and not limitation, membranes having various thicknesses and shapes described herein were evaluated. In one example, three different membrane shapes were developed and multiple thicknesses were evaluated with each shape. A thickness of 0.013" was chosen to improve the flow rate efficiency of the Elastollan S95A55N, while being suitable to manufacture and allow for acceptable wear. As shown in Table 1, the flow rate difference between the glued membrane versus a membrane supported by a rib was reduced with the additional curvatures at the inlet and outlet portions of the membrane (e.g., as illustrated in the configuration of FIGS. 11H and 11I). As illustrated herein, the addition of the rib provided an improved joint and reduced impact on flow rate due to relaxation of the glue joint. In Table 1, for example and without limitation, inlet and outlet curvatures in membrane 37 configured with a support rib 108, as shown for example and without limitation in FIG. 11E, provided the highest flow rate of material through the peristaltic tube 23.

TABLE 1

| Membrane Sample | Flow rate |
| --- | --- |
| No membrane | 25.63 |
| 1. Rib + Membrane with no additional curve (e.g., FIG. 11F and 11G) | 21.74 |
| 2. Glue + Membrane with no additional curve (e.g., FIG. 11F and 11G) | 20.40 |
| 3. Rib + Membrane with Inlet and Outlet Curves (e.g., FIG. 11H and 11I) | 24.24 |

For the purpose of understanding and not limitation, reference is made to Tables 2-3 and FIGS. 11H to 11Q as various operational characteristics achieved by different membrane configurations disclosed herein. In one test, shown in Table 2, finite element analysis was performed to simulate material flow through a peristaltic tube, depending on the shape of membrane 37. Similar to the results of Table 1, membrane 37d (Sample 1) having inlet curves 109a and outlet curves 109b, as illustrated in FIGS. 11H and 11I, had the average flow rate as compared to other simulations of other membrane shapes, including membrane 37e with inlet curve only 109a as shown in membrane 37f of FIGS. 11L and 11M (Sample 3) and membrane 37 with no additional curvatures (Sample 4). As such, an increase in the number of curves added to membrane 37 did not necessarily improve flow rate or efficiency. For example, membrane 37g (Sample 5) illustrated at FIGS. 11N and 11O included two bellows 110b along the length of the membrane 37g, and membrane 37h (Sample 6) illustrated at FIGS. 11P and 11Q included three bellows 110c along the width of membrane 37h. For example and not limitation, the two bellows 110b can each have a radius of curvature of around 8-12 mm or 10 mm as embodied in FIG. 11N. The bellows 110c can each have a radius of curvature of around 1-2 mm or 1.5 mm as embodied in FIG. 11Q. Other curvature values may be possible. As shown for example in Table 2 Samples 5 and 6 did not provide improved flow efficiency relative to, for example, Sample 1. In another test, as shown in Table 3, physical testing of membrane 37 was performed. In this example, the volume of material per time flowing through peristaltic tube 23 was measured against the volume of material per time flowing through peristaltic tube 23 without a membrane. Similar to Table 2, membrane of FIGS. 11H and 11I, having inlet curves 109a and outlet curves 109b provided the closest volume of flow material per time through tube 23 as compared to the pump with no membrane.

TABLE 2

Finite Element Analysis

| Membrane Sample | Packet Size (uL/rev) | Efficiency Relative to "No Membrane-Test" Case |
| --- | --- | --- |
| No Membrane | 20.9 | 100% |
| 1. Membrane with inlet and outlet curves (e.g., FIGS. 11H and 11I | 19.2 | 92% |
| 2. Membrane without curves, top and bottom slits | 18.2 | 87% |
| 3. Membrane with inlet curve only (e.g., FIGS. 11L and 11M) | 17.8 | 85% |
| 4. Membrane without curves (e.g., FIGS. 11F and 11G) | 17.2 | 82% |
| 5. Membrane with bellow along length (e.g., FIGS. 11N and 11O) | 18.4 | 88% |
| 6. Membrane with bellow along width (e.g., FIGS. 11P and 11Q) | 16.5 | 79% |

TABLE 3

Physical testing

| Membrane Sample | Packet Size (uL/rev) | Efficiency Relative to "No Membrane-Test" Case |
| --- | --- | --- |
| No Membrane | 19.1 | 100% |
| 1. Membrane with inlet and outlet curves (e.g., FIG. 11H and 11I) | 18.3 | 96% |
| 2. Membrane with only inlet curve (e.g., FIG. 11L and 11M) | 16.4 | 86% |
| 3. Membrane without curve (e.g., FIGS. 11F and 11G) | 15.4 | 81% |

Figure 11R:
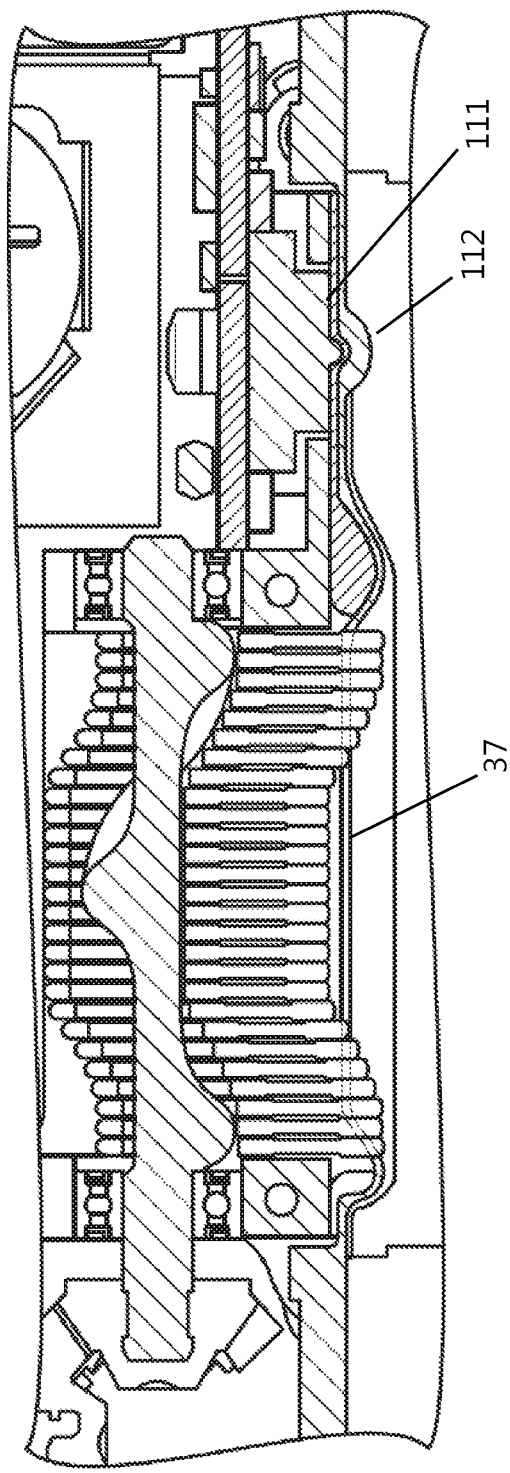
FIG. 11R is a top view of an exemplary configuration of a membrane and occlusion sensor in a pump assembly, in accordance with the disclosed subject matter.

Referring now to FIG. 11R, a cross-section of membrane 37, finger plates 34, and occlusion sensor 111 illustrates additional features of membrane 37. For example, and as embodied herein, the base cassette region can be received in the receiving region 32, and the peristaltic tube can engage an occlusion sensor 111 proximate to the rear closure portion 35. The occlusion sensor 111 can be configured to detect a stop in fluid flow through the peristaltic tube. For example and as embodied herein, occlusion sensor 111 can include a pressure sensor. Membrane 37 can be disposed over the occlusion sensor 111, which can protect the occlusion sensor 111 from debris, and include an occlusion sensor protrusion 112 configured to surround at least a portion of the occlusion sensor 111. The occlusion sensor protrusion 112 can have a thickness greater than a remainder of the membrane. For example and as embodied herein, the occlusion sensor protrusion 112 can have a thickness of 0.037" such that the region of the membrane 37 closest to the occlusion sensor 111 was thickened over the sensor 111. For example, and as embodied herein, the remainder of the membrane can have a thickness of 0.013".

Figure 12A:
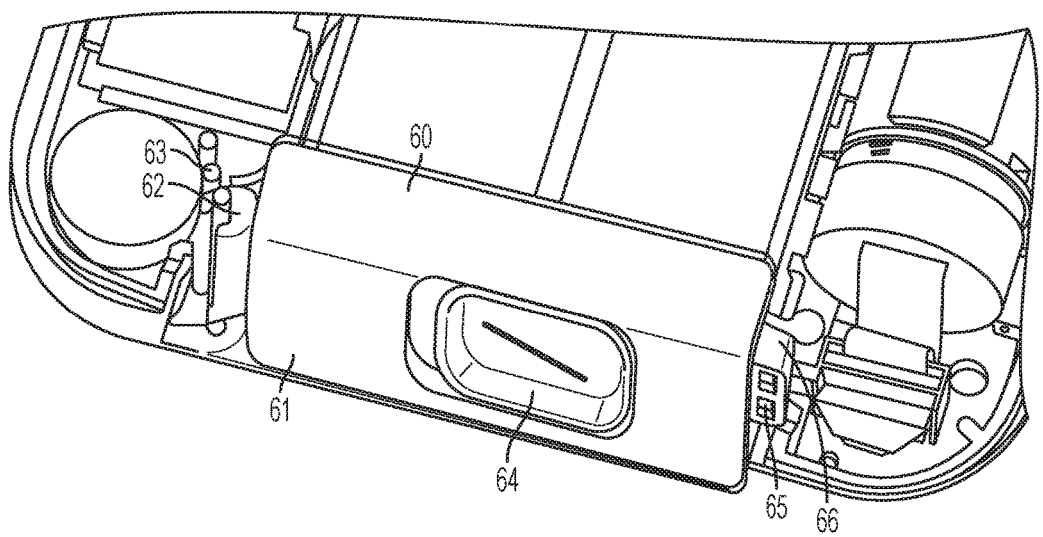
FIG. 12A is a top perspective view of an exemplary battery cover door of the pump of FIG. 1, with the battery cover door in a closed position, and selected portions cut away for purpose of illustration.
Figure 12B:
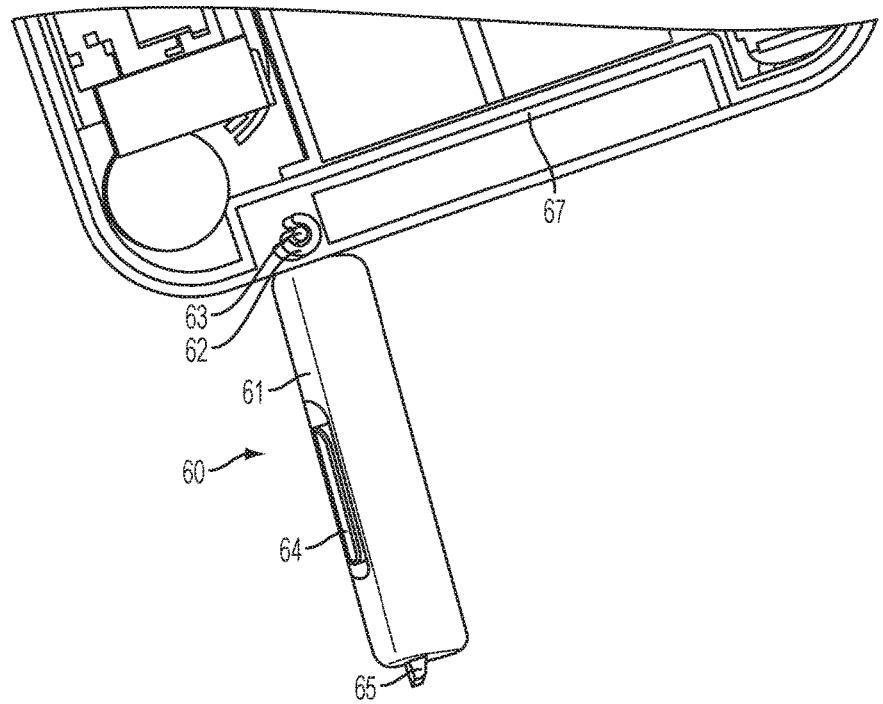
FIG. 12B is a top view of the exemplary battery cover door of FIG. 12A, with the battery cover door in an open position, and selected portions cut away for purpose of illustration.

Referring now to FIGS. 12A-12B, for the purpose of illustration and not limitation, in some embodiments, the pump housing 31 can include a battery cover 611. The battery cover 61 can have a rectangular shape defining a length and width. In some embodiments, the battery cover 61 can be hingedly connected to the pump housing 31 along the width (referred to as a "barn door arrangement"). In alternative embodiments battery cover 61 can be hingedly connected to the pump housing 31 along the length (referred to as a "tailgate arrangement"). FIGS. 12A-12B show the battery cover 61 in the barn door arrangement. As embodied herein, the pump housing 31 can include a rod 63. The battery cover 61 can include a hinge 62 having a 'C' shape. The C-shaped hinge 62 can allow the battery cover 61 to snap off of the pump housing 31 if urged too far away from the pump housing 31 without damaging the hinge and allowing the battery cover 61 to be reinstalled. In this manner, preventing damage to the battery cover 61 from over extension of the battery cover can provide a benefit for a user with poor dexterity. Battery cover 61 can include a release button 64 coupled to a latch projection 65. Actuation of release button 64, for example by sliding release button away from latch projection 65, can release latch projection from a latch receptacle 66 in pump housing 31 to allow hinged movement of battery cover 61 away from pump housing 31. The battery compartment can also include a gasket to insulate the battery compartment and protect the battery compartment from fluid ingress.

Figure 13:
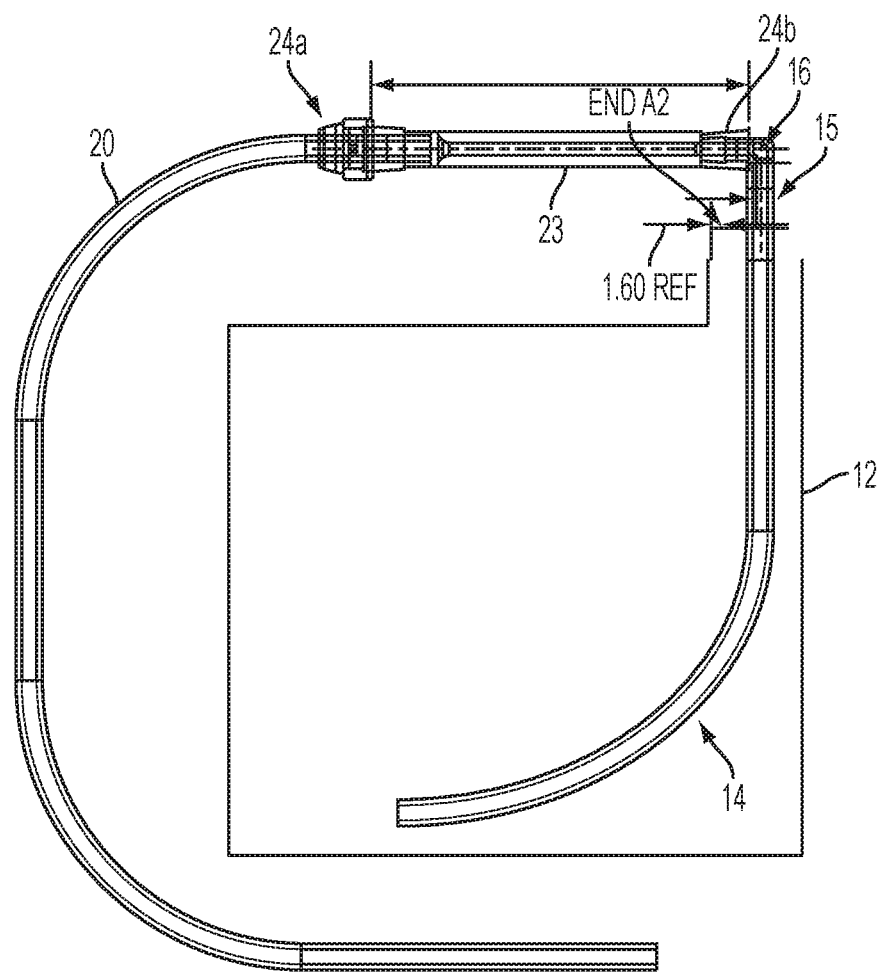
FIG. 13 is a plan view of an exemplary delivery tube assembly and fluid reservoir for use with the disclosed subject matter.

Referring now to FIG. 13, as embodied herein, cassette housing 11 can contain a fluid reservoir therein. For example, the housing itself can define the fluid reservoir, or an additional component to define the reservoir can be contained therein. If provided separately, the fluid reservoir 12 can be disposed in the cassette housing 11. For example, and as embodied herein, the cassette housing 11 can be configured with two enclosure clamshell portions 17 and 18 (as shown for example in FIGS. 1-3), which can receive and contain the fluid reservoir 12. The two clamshell portions 17 and 18 can be adhered or otherwise joined together, for example by ultrasonic welding.

As embodied herein, fluid reservoir 12 can include a flexible pouch, which can have any of a variety of suitable shapes. Opposing sides of the pouch can be secured about a perimeter to form the fluid reservoir 12, for example by thermal or radio frequency (RF) welding or the like. The fluid reservoir 12 can have a dip tube 14. The dip tube 14 can be configured, for example and without limitation, from SUNLITE VYSUN 102-80-26 (Non-DEHP PVC), DuPont Elvax 3182-2 EVA, or any suitable tubing material. As embodied herein, the dip tube 14 can have a length within a range of approximately 108-111 mm, with a plurality of approximately 2 mm diameter apertures disposed therein. The dip tube 14 can extend from the fluid reservoir 12 to serve as a delivery tube if desired or appropriate. Alternatively, and as embodied herein, an adaptor disposed external to the cassette housing 11 can be provided and coupled to a proximal end of the dip tube 14. In this manner, a separate delivery tube can be coupled to the adaptor for delivery of the beneficial agent from the fluid reservoir 12 to the user by operation of the pump 30. Additionally, a peristaltic tube can be provided between or as a part of the dip tube 14 and/or the delivery tube for interaction with the pump 30.

For the purpose of illustration and not limitation, an exemplary embodiment of such an adaptor is depicted in FIG. 13. As shown, the fluid reservoir 12 includes an adaptor 15 disposed external to the cassette housing 11. Adaptor 15 can be coupled to a proximal end of the dip tube 14. As embodied herein, a polypropylene-barbed elbow fitting 16 is provided at the proximal end of the dip tube 14. The elbow fitting 16 can be adhered to the exterior end of the dip tube 14 and oriented in plane with the fluid reservoir 12. A peristaltic tube 23 can be installed or coupled to an opposing end of the elbow fitting 16. For example, and as embodied herein, the peristaltic tube 23 can be formed from a section of Saint Gobain Biosil Precision tubing material. The peristaltic tube 23 can have an inside diameter of 1.6 mm and an outside diameter of 4.8 mm. A junction fitting 24 is joined to the peristaltic tube 23, and a delivery tube 20 can be adhered into the junction fitting 24. As such, the delivery tube 20 can be fluidly coupled with the fluid reservoir 12.

Each of the components described herein can be made of any suitable material (e.g., plastic, composites, metal, etc.) and technique for its intended purpose. In addition to the specific embodiments claimed below, the disclosed subject matter is also directed to other embodiments having any other possible combination of the dependent features claimed below and those disclosed above. As such, the particular features disclosed herein can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

The devices and techniques of the disclosed subject matter can be used for delivery of any of a variety of suitable fluid substances of corresponding volume or dose.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A device for delivering a beneficial agent, comprising:
a pump including a pump housing containing a pump assembly having a fluid drive component, the pump housing having a receiving region disposed proximate the fluid drive component, the pump housing comprising a rear closure portion including a membrane disposed between the receiving region and the fluid drive component; and
a cassette including a cassette housing comprising a cassette body region defining a fluid reservoir chamber therein and a delivery tube assembly extending from the fluid reservoir chamber, the cassette further including a cassette base region having a boundary configured to be received by the receiving region;
wherein the delivery tube assembly comprises a peristaltic tube that engages an occlusion sensor proximate the rear closure portion when the cassette base region boundary is received by the receiving region, and the membrane includes an occlusion sensor protrusion configured to cover a portion of the occlusion sensor.

2. The device of claim 1, wherein the rear closure portion includes a slot proximate a lateral edge of the receiving region, the membrane being molded over the slot and defining a protrusion extending to said lateral edge of the receiving region.

3. The device of claim 2, wherein the slot comprises a plurality of edges to support the membrane, the membrane being molded over the edges.

4. The device of claim 2, wherein the fluid chive component comprises a plurality of finger plates disposed along a length of a cam shaft and configured to protrude from the slot to engage an interior surface of the membrane during rotation of the cam shaft.

5. The device of claim 1, wherein the receiving region includes a support rib proximate to the rear closure portion, the membrane being molded over the support rib.

6. The device of claim 1, wherein the fluid drive component comprises a plurality of finger plates configured to push on the peristaltic tube with the membrane disposed between the plurality of finger plates and the peristaltic tube.

7. The device of claim 1, wherein the membrane has a curvature corresponding to a curvature of the peristaltic tube.

8. The device of claim 1, wherein the peristaltic tube is secured at an inlet end and an outlet end thereof, the membrane having a curvature proximate the inlet end and the outlet end corresponding to a position of the finger plates when the peristaltic tube is engaged by the finger plates at the inlet end and the outlet end.

9. The device of claim 1, wherein the occlusion sensor protrusion comprises a portion of the membrane positioned over the occlusion sensor having a thickness greater than adjacent portions of the membrane.

10. The device of claim 1, wherein the membrane comprises Elastollan S95A55N material.

11. The device of claim 1, comprising a lock member coupled to the pump housing and movable between an open position and a closed position, the cassette capable of being inserted into and removed from the receiving region when the lock member is in the open position, and the cassette being secured to the pump with the cassette base region within the receiving region.

12. The device of claim 11, comprising a delivery tube fluidly coupled with the fluid reservoir, wherein a length of the delivery tube is operatively engaged with the fluid drive component when the lock member is in the closed position.

* * * * *